US 9,527,064 B2

United States Patent
Akagishi et al.

(10) Patent No.: US 9,527,064 B2
(45) Date of Patent: Dec. 27, 2016

(54) SILICA COMPOSITE, METHOD FOR PRODUCING THE SAME, AND METHOD FOR PRODUCING PROPYLENE USING THE SILICA COMPOSITE

(75) Inventors: Kenji Akagishi, Tokyo (JP); Ryusuke Miyazaki, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 603 days.

(21) Appl. No.: 13/818,113

(22) PCT Filed: Nov. 24, 2011

(86) PCT No.: PCT/JP2011/077007
§ 371 (c)(1),
(2), (4) Date: Feb. 28, 2013

(87) PCT Pub. No.: WO2012/070605
PCT Pub. Date: May 31, 2012

(65) Prior Publication Data
US 2013/0231515 A1  Sep. 5, 2013

(30) Foreign Application Priority Data

Nov. 25, 2010  (JP) .................. 2010-262752

(51) Int. Cl.
| | |
|---|---|
| B01J 29/06 | (2006.01) |
| B01J 29/40 | (2006.01) |
| C07C 1/20 | (2006.01) |
| C07C 2/00 | (2006.01) |
| C07C 11/06 | (2006.01) |
| B01J 29/80 | (2006.01) |
| B01J 29/90 | (2006.01) |
| B01J 35/00 | (2006.01) |
| B01J 35/08 | (2006.01) |
| C10G 3/00 | (2006.01) |
| B01J 37/00 | (2006.01) |
| B01J 37/28 | (2006.01) |
| B01J 29/70 | (2006.01) |
| B01J 29/85 | (2006.01) |

(52) U.S. Cl.
CPC .............. *B01J 29/40* (2013.01); *B01J 29/06* (2013.01); *B01J 29/80* (2013.01); *B01J 29/90* (2013.01); *B01J 35/002* (2013.01); *B01J 35/0026* (2013.01); *B01J 35/08* (2013.01); *B01J 37/0045* (2013.01); *C07C 1/20* (2013.01); *C07C 2/00* (2013.01); *C07C 11/06* (2013.01); *C10G 3/49* (2013.01); *B01J 29/7015* (2013.01); *B01J 29/85* (2013.01); *B01J 37/0009* (2013.01); *B01J 37/0036* (2013.01); *B01J 37/28* (2013.01); *B01J 2229/10* (2013.01); *B01J 2229/186* (2013.01); *B01J 2229/37* (2013.01); *B01J 2229/42* (2013.01); *C07C 2529/40* (2013.01); *C07C 2529/85* (2013.01); *Y02P 20/52* (2015.11); *Y02P 20/584* (2015.11); *Y02P 30/42* (2015.11)

(58) Field of Classification Search
USPC ........................................ 502/64, 71, 85, 86
See application file for complete search history.

(56) References Cited

U.S. PATENT DOCUMENTS

| | | | |
|---|---|---|---|
| 2001/0053868 | A1 | 12/2001 | Chester et al. |
| 2009/0134065 | A1 | 5/2009 | Cheng et al. |
| 2010/0197986 | A1 | 8/2010 | Midorikawa et al. |

FOREIGN PATENT DOCUMENTS

| | | |
|---|---|---|
| CN | 1370216 A | 9/2002 |
| CN | 101213269 A | 7/2008 |
| CN | 101772476 A | 7/2010 |
| EP | 0496226 A1 | 7/1992 |
| EP | 2311561 A1 | 4/2011 |
| JP | 2003-504500 A | 2/2003 |
| JP | 2007-244964 A | 9/2007 |
| JP | 2009-500153 A | 1/2009 |
| JP | 2009-221030 A | 10/2009 |
| JP | 2010-247146 A | 11/2010 |

OTHER PUBLICATIONS

Chinese Office Action and Search Report for Chinese Application No. 201180056427.8, dated Apr. 24, 2014.
International Search Report issued in PCT/JP2011/077007 mailed Feb. 7, 2012.
European Search Report, dated Mar. 23, 2015, for European Application No. 11843607.0.

*Primary Examiner* — Elizabeth Wood
(74) *Attorney, Agent, or Firm* — Birch, Stewart, Kolasch & Birch, LLP

(57) ABSTRACT

The present invention provides a method for producing a silica composite by the steps of:
 preparing a raw material mixture containing silica and zeolite;
 drying the raw material mixture to obtain a dried product; and
 calcining the dried product,
 wherein the method comprising the step of allowing the raw material mixture to contain phosphoric acid and/or phosphate or bringing a solution of phosphoric acid and/or phosphate into contact with the zeolite and/or the dried product, or a combination thereof to thereby adjust a phosphorus content in the silica composite to 0.01 to 1.0% by mass based on the total mass of the silica composite.

6 Claims, 9 Drawing Sheets

SILICA COMPOSITE, METHOD FOR PRODUCING THE SAME, AND METHOD FOR PRODUCING PROPYLENE USING THE SILICA COMPOSITE

TECHNICAL FIELD

The present invention relates to a silica composite containing phosphorus, a method for producing the same, and a method for producing propylene using the silica composite.

BACKGROUND ART

Lower olefins such as ethylene, propylene, and butene serve as important, principal raw materials for chemical industry. Particularly, various methods for producing propylene have been developed and modified actively in recent years, in expectation of significant growth in demand therefor. Propylene is mainly produced by the thermal cracking of naphtha or by the catalytic cracking of heavy petroleum distillate using a catalyst. Its reaction scheme is composed mainly of a fluidized-bed reaction using zeolite of USY or MFI type as a catalyst. These catalysts are sometimes inactivated due to heavy carbonaceous materials (coke) accumulating in zeolite pores as a result of reaction with hydrocarbon. Therefore, the catalysts require, for their regeneration, removing coke by combustion in an atmosphere containing oxygen. However, this coke combustion generates water which disadvantageously causes aluminum as an active site in the crystal lattice of zeolite to be eliminated from the crystal lattice, leading to reduced catalyst performance.

Moreover, the production of propylene using zeolite with methanol, ethanol (particularly, bioethanol produced with a plant as a raw material), or dimethyl ether as a raw material has also been studied as a method without the use of petroleum as a raw material. In this case as well, the dealumination of zeolite disadvantageously occurs due to high-temperature steam formed during this reaction, resulting in reduced catalyst performance.

For the purpose of overcoming these disadvantages or further improving the selectivity of an objective substance, a method for modifying zeolite with a phosphorus compound has been studied variously.

For example, Patent Literature 1 discloses a catalyst composition for fluid catalytic cracking of spherical hydrocarbon microparticles consisting of 5 to 20% by weight of $P_2O_5$, 10 to 50% by weight of zeolite of pentasil type, and 30 to 85% by weight of porous inorganic oxide, and a method for producing the same.

Moreover, Patent Literature 2 discloses a fluidized-bed reaction catalyst comprising pentasil zeolite, at least 5% by weight of $P_2O_5$, and at least 1% by weight of $F_2O_3$ and having an average particle size of 20 to 200 μm, and a method for producing the same.

Furthermore, Patent Literature 3 discloses a catalyst consisting of ZSM-5 and/or ZSM-11, phosphorus, and a substantially inactive matrix substance, the catalyst being used in a method for producing a light olefin and an aromatic compound from $C_4^+$ naphtha hydrocarbon, and a method for producing the same.

CITATION LIST

Patent Literature

[Patent Literature 1] Japanese Patent Laid-Open No. 2007-244964
[Patent Literature 2] National Publication of International Patent Application No. 2009-500153
[Patent Literature 3] National Publication of International Patent Application No. 2003-504500

SUMMARY OF INVENTION

Problems to be Solved by the Invention

However, the present inventors have revealed that stainless steel, which is routinely used in industrial apparatuses, significantly corrodes, as a result of using catalysts produced according to Examples of Patent Literatures 1 to 3 above to conduct the corrosion test of the stainless steel in an atmosphere containing high-temperature steam that would be present in a catalyst regenerator, a reactor, or the like. This is very seriously disadvantageous to the industrial use of catalysts.

In view of the circumstances, an object of the present invention is to provide a silica composite that is hardly subject to dealumination of zeolite even in a high-temperature steam atmosphere and causes less corrosion of stainless steel routinely used in industrial apparatuses, a method for producing the same, and a method for producing propylene using the silica composite.

Means for Solving the Problems

The present inventors have conducted diligent studies to attain the object and consequently completed the present invention by finding that the object can be attained by a silica composite that contains phosphorus, zeolite, and silica and is produced by a particular method with a phosphorus content adjusted to a particular range.

Specifically, the present invention is as follows:

[1]
A method for producing a silica composite comprising the steps of:
preparing a raw material mixture containing silica and zeolite;
drying the raw material mixture to obtain a dried product; and
calcining the dried product,
wherein the method comprising the step of allowing the raw material mixture to contain phosphoric acid and/or phosphate or bringing a solution of phosphoric acid and/or phosphate into contact with the zeolite and/or the dried product, or a combination thereof to thereby adjust a phosphorus content in the silica composite to 0.01 to 1.0% by mass based on the total mass of the silica composite.

[2]
The method for producing the silica composite according to [1], wherein the step of bringing the solution of phosphoric acid and/or phosphate into contact with the zeolite and/or the dried product comprises adjusting the amount of the solution of phosphoric acid and/or phosphate so that the zeolite and/or the dried product maintain their powdery states.

[3]
The method for producing the silica composite according to [1] or [2], further comprising the step of pulverizing the zeolite after the step of bringing the solution of phosphoric acid and/or phosphate into contact with the zeolite.

[4]

The method for producing the silica composite according to any of [1] to [3], wherein a source of the phosphorus is phosphate.

[5]

The method for producing the silica composite according to any of [1] to [4], wherein the phosphorus content in the silica composite is 0.01 to 0.5% by mass based on the total mass of the silica composite.

[6]

The method for producing the silica composite according to any of [1] to [5], wherein the zeolite is of MFI type and has a $SiO_2/Al_2O_3$ ratio (by mol) of 20 or more.

[7]

The method for producing the silica composite according to any of [1] to [6], further comprising the step of bringing a calcined product obtained in the calcining step into contact with an acidic liquid after calcining the dried product.

[8]

The method for producing the silica composite according to any of [1] to [7], wherein the silica composite is substantially free from aluminum.

[9]

A method for producing propylene comprising the step of Producing a silica composite by the production method according to any one of claims 1 to 8, bringing the silica composite into contact with a hydrocarbon source containing at least one component selected from the group consisting of ethylene, ethanol, methanol, and dimethyl ether in the presence of steam.

[10]

The method for producing propylene according to [9], wherein the reaction is performed using a fluidized-bed reactor.

[11]

The method for producing propylene according to [9] or [10], wherein the reaction is performed at a WHSV of 0.1 to 1.0 $h^{-1}$.

[12]

The method for producing propylene according to any of [9] to [11], wherein the hydrocarbon source contains 50% by mass or more of ethylene.

[13]

A silica composite produced by the production method according to any of [1] to [8].

[14]

The silica composite according to [13], wherein the silica composite has a stainless steel corrosion index of 10000 or lower.

[15]

A catalyst comprising the silica composite according to [13] or [14],

Wherein the catalyst being intended for the production of propylene by bringing the catalyst into contact with a hydrocarbon source containing at least one component selected from the group consisting of ethylene, ethanol, methanol, and dimethyl ether in the presence of steam.

Advantageous Effects of Invention

A silica composite obtained by a production method of the present invention is hardly subject to dealumination of zeolite in a high-temperature steam atmosphere and causes less corrosion of stainless steel. Therefore, the silica composite is preferable as a catalyst in a reaction to produce propylene in the presence of steam from a hydrocarbon source containing at least one component selected from the group consisting of ethylene, ethanol, methanol, and dimethyl ether. The silica composite further has excellent properties (favorable shape and sufficient attrition resistance) as a fluidized-bed reaction catalyst and as such, is preferable for fluidized-bed reaction catalyst use.

MODE FOR CARRYING OUT THE INVENTION

Figure 1:
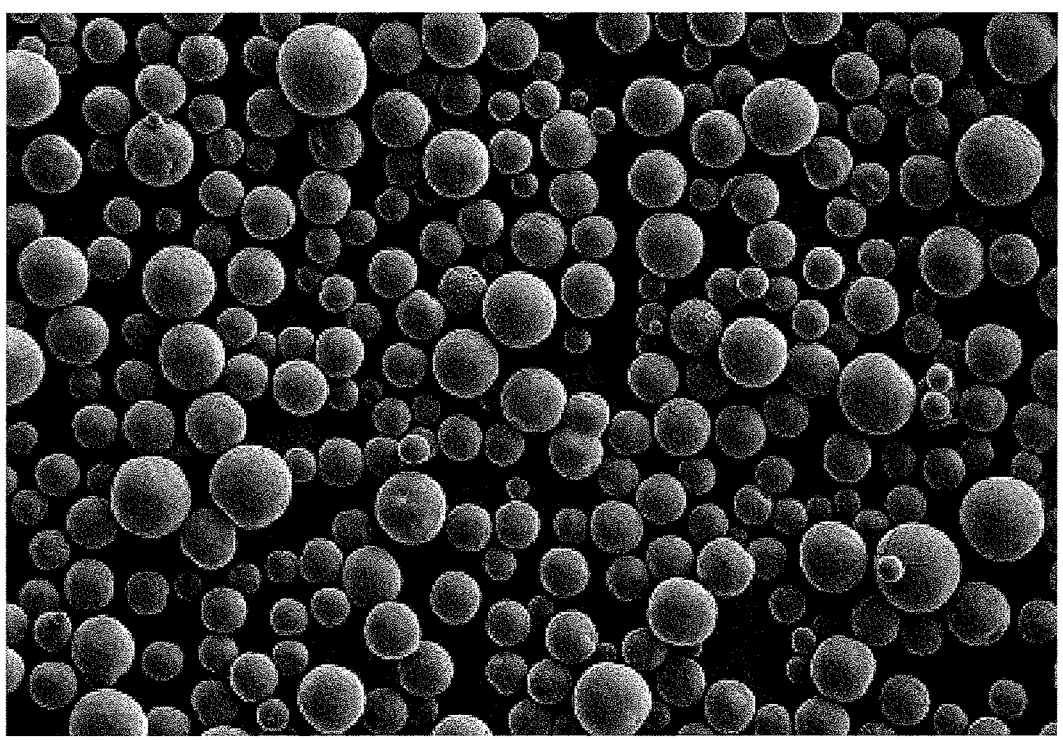
FIG. 1 shows an electron micrograph of a silica composite of Example 1 (magnification: 150 times).

Hereinafter, the mode for carrying out the present invention (hereinafter, referred to as the "present embodiment") will be described in detail. The present invention is not limited to the present embodiment described below, and various changes or modifications can be made without departing from the spirit thereof.

The term "silica" used herein refers to silica used as a support of a silica composite and does not mean silica constituting zeolite or clay mineral, unless otherwise specified. Likewise, the term "alumina" refers to alumina used as a support of a silica composite and does not mean alumina constituting zeolite or clay mineral, unless otherwise specified.

A method for producing a silica composite according to the present embodiment is a method for producing a silica composite by the steps of:

preparing a raw material mixture containing silica and zeolite;

drying the raw material mixture to obtain a dried product; and calcining the dried product, wherein the method comprising the step of allowing the raw material mixture to contain phosphoric acid and/or phosphate or bringing a solution of phosphoric acid and/or phosphate into contact with the zeolite and/or the dried product, or a combination thereof to thereby adjust a phosphorus content in the silica composite to 0.01 to 1.0% by mass based on the total mass of the silica composite.

[Silica Composite]

A silica composite obtained by the method for producing a silica composite according to the present embodiment will be described.

The silica composite according to the present embodiment contains phosphorus, zeolite, and silica. The silica composite may be used as a catalyst in a reaction to produce propylene from a hydrocarbon source containing at least one component selected from the group consisting of ethylene, ethanol, methanol, and dimethyl ether (hereinafter, also simply referred to as "propylene production reaction"). Examples of preferable zeolite contained in such a silica composite include zeolite having a three-dimensional pore structure. Examples of such zeolite having a three-dimensional pore structure include MFI type such as ZSM-5, silicalite, and TS-1, and CHA type such as chabazite, ALPO-34, and SAPO-34. The zeolite is preferably of MFI type having an intermediate pore size on the order of approximately 0.51 to 0.56 nm, particularly preferably ZSM-5 because of its high heat resistance, shape selectivity, and characteristic catalytic activity attributed to strong solid acidity.

In this context, the terms "MFI" and "CHA" refer to the classification codes of zeolite specified based on its structure by the International Zeolite Association (IZA).

The $SiO_2/Al_2O_3$ ratio (by mol) of the zeolite is preferably 20 or more, more preferably in the range of 20 to 10000, further preferably 20 to 1000, still further preferably 20 to 500, particularly preferably 200 to 500. Zeolite having a $SiO_2/Al_2O_3$ ratio (by mol) less than 20 has too many aluminum atoms as an active site in its lattice. This tends to facilitate zeolite deactivation by coking during propylene production reaction.

Preferably, the zeolite has a relatively high $SiO_2/Al_2O_3$ ratio (by mol) because such zeolite tends to enhance propylene yields when used as a catalyst in propylene production reaction. This zeolite further tends to reduce the formation of a by-product propane. This can advantageously lighten the load on the purification step of separating propylene and propane having similar boiling points and is thus of great industrial value. Zeolite containing no or a very trace amount of $Al_2O_3$ is called "silicalite" which has no or very few acidic centers attributed to aluminum. Depending on use of the silica composite, silicalite may be more preferable than those having a small $SiO_2/Al_2O_3$ ratio (by mol). A typical example thereof is use as a catalyst in the production of caprolactam. On the other hand, a lower aluminum content tends to result in higher propylene selectivity in propylene production reaction and, on the contrary, reduces catalytic activity. Thus, the upper limit of the $SiO_2/Al_2O_3$ ratio is preferably approximately 10000. Accordingly, the $SiO_2/Al_2O_3$ ratio can be set to an appropriate value depending on use of the silica composite. Thus, the preferable value of the upper limit is not universalized.

The zeolite includes aluminosilicate such as ZSM-5 as well as metallosilicate with a structure having other metal atoms (e.g., gallium, iron, boron, titanium, and vanadium) substituted for the aluminum atoms in the skeleton.

When metallosilicate is used as the zeolite, the $SiO_2/Al_2O_3$ ratio (by mol) is calculated by taking into consideration the metal atoms substituted for the aluminum atoms in the zeolite skeleton, instead of the aluminum atoms. For example, silicoaluminophosphate such as SAPO-34 may be used as the zeolite. In such a case, since its structure has Si atoms substituted for a portion of $AlO_4$ and $PO_4$ in the skeleton, the $SiO_2/Al_2O_3$ ratio (by mol) is defined as (Al+P)/Si (atomic ratio).

Preferably, the zeolite has high crystallinity because such zeolite tends to be hardly subject to dealumination in a high-temperature steam atmosphere. The crystallinity of the zeolite can be determined by powder X-ray diffractometry. The term "high crystallinity" means high diffraction intensity determined at a diffraction angle in the range of 5 to 50 degrees by a routine method. In general, zeolite crystals having definite ridges in their crystal forms, such as a hexagonal plate-like or cubic form, tend to have high diffraction intensity, rather than spherical crystals.

The zeolite content in the silica composite of the present embodiment is preferably 15 to 65% by mass, more preferably 30 to 60% by mass, based on the total mass of the silica composite from the viewpoint of obtaining sufficient activity.

Preferably, the silica composite contains only MFI type as the zeolite, when used as a catalyst in propylene production reaction. However, other zeolites such as SAPO-34 (CHA), Y type (FAU), ultrastable Y type (FAU), mordenite (MOR), and beta type (BEA) may coexist therewith without adversely affecting propylene production reaction. The zeolite contained in the silica composite comprises preferably 60% by mass or more, more preferably 80% by mass or more of MFI type, based on the total mass of the zeolite.

The silica composite according to the present embodiment contains silica. It is not essential that the silica in the silica composite consists only of silica having pure $SiO_2$ composition. The silica can be any silica contained in an inorganic porous support composed mainly of silica. The phrase "inorganic porous support mainly composed of silica" means that the inorganic porous support contains 60% by mass or more, preferably 80% by mass or more of silica based on the total mass of the support (the support is defined as a component except for zeolite and phosphorus in the silica composite). An inorganic porous support containing a large amount of silica is preferable because the resulting silica composite tends to have high attrition resistance. The inorganic porous support may contain, for example, clay mineral (e.g., kaolin), zirconia, titania, and/or ceria as the remaining portion other than silica. Their contents are preferably 20% by mass or less, more preferably 10% by mass or less, particularly preferably 0% by mass (i.e., the support consists only of silica), based on the total mass of the support. In the case of a silica composite for industrial catalyst use, a form consisting only of zeolite is not generally practical due to insufficient catalyst strength.

When the silica composite according to the present embodiment is used as a catalyst in propylene production reaction, its form is, more preferably, substantially free from aluminum such as alumina. The term "substantially free from aluminum" means that the silica composite does not contain aluminum in an amount that adversely affects its physical properties or propylene yields in the reaction. However, this aluminum does not mean aluminum contained in the zeolite skeleton. Specifically, its aluminum content is preferably less than 5% by mass in terms of alumina. A silica composite containing aluminum in an amount exceeding 5% by mass based on the total mass of the silica composite tends to reduce propylene yields in the reaction. In addition, such a silica composite tends to have the low smoothness of particle surface and low attrition resistance and is thus prone to be poorly flowable and fragile when used as a catalyst in fluidized-bed reaction.

The support content in the silica composite according to the present embodiment is preferably 35 to 85% by mass, more preferably 40 to 70% by mass, based on the total mass of the silica composite. A silica composite having a support content less than 35% by mass tends to have low attrition resistance. On the other hand, a silica composite having a support content exceeding 85% by mass tends to have low activity due to the low content of zeolite serving as an active ingredient.

The silica composite according to the present embodiment contains phosphorus. Examples of forms of the phosphorus include polymers of phosphorus (e.g., polyphosphoric acid), oxides of phosphorus (e.g., $P_2O_5$), and compounds in the form of phosphorus added to aluminum in zeolite. The silica composite may contain some of these forms.

The phosphorus has the effect of inhibiting the dealumination of zeolite containing aluminum and, in some cases, the effect of improving propylene yields in propylene production reaction. Particularly, in the case of a silica composite for use exposed to a high-temperature steam atmosphere, the effects of the phosphorus become more pronounced because the properties of such a silica composite are easily altered due to dealumination.

The phosphorus content in the silica composite is 0.01 to 1.0% by mass, preferably 0.01 to 0.5% by mass, more preferably 0.01 to 0.3% by mass, further preferably 0.05 to 0.3% by mass, particularly preferably 0.1 to 0.3% by mass, based on the total mass of the silica composite. Phosphorus at a content less than 0.01% by mass has the small effect of inhibiting the dealumination of zeolite in a high-temperature steam atmosphere. On the other hand, phosphorus at a content exceeding 1.0% by mass is more likely to cause the corrosion of stainless steel in a high-temperature steam atmosphere.

In the present embodiment, the phosphorus content in the silica composite refers to a value measured using an X-ray fluorescence analyzer. The phosphorus content can be measured under usual conditions using a commercially available X-ray fluorescence analyzer according to the instruction manual. For example, measurement conditions can be set to a tube voltage of 50 kV and a tube current of 50 mA with P-Kα rays using, for example, "RIX3000" (trade name) manufactured by Rigaku Corp.

The silica composite according to the present embodiment may be contained in a stainless steel container. For such use, its corrosion index is preferably 10000 or lower, more preferably 8000 or lower, from the viewpoint of protecting stainless steel. In the present embodiment, the corrosion index which represents the corrosive effect on stainless steel refers to a value measured by the following method.

The silica composite is pulverized into 6- to 16-mesh particles, and 12 g of the particles is loaded, together with a stainless steel (SUS304) specimen (20 mm×10 mm, thickness: 1 mm), into a quartz reaction tube. The specimen is kept at 550° C. for 7 days in the reaction tube with gasses circulated (steam: 80 vol % and nitrogen: vol %). The resulting specimen after the test is observed under a microscope, and the corrosion index is determined according to the following equation:

Corrosion index=the number of corrosion pits (pits/cm²)×average size of corrosion pits (μm)×average depth of corrosion (μm)

In this context, the number of corrosion pits is determined by counting the number of pits formed by corrosion per cm² of a specimen. The average size of corrosion pits is determined by measuring the size of pits formed by corrosion and determining the arithmetic mean thereof. The average depth of corrosion is determined by cutting a specimen, measuring the depth of pits formed by corrosion in the obtained cross section, and determining the arithmetic mean thereof.

In this context, the term "corrosion" refers to a phenomenon in which a metal is destroyed by alteration through chemical or electric reaction.

The combination of the $SiO_2/Al_2O_3$ ratio (by mol) of the zeolite and the phosphorus content in the silica composite is preferably a $SiO_2/Al_2O_3$ ratio (by mol) of 20 to 1000 in zeolite and a phosphorus content of 0.05 to 1.0% by mass, more preferably a $SiO_2/Al_2O_3$ ratio (by mol) of 200 to 1000 and a phosphorus content of 0.05 to 0.3% by mass, for use in propylene production reaction from the viewpoint of reducing corrosive effect while maintaining high catalyst performance.

In the present embodiment, phosphoric acid and/or phosphate (hereinafter, also referred to as a "phosphorus source") is used as a source of the phosphorus contained in the silica composite. In this context, the "phosphate" (salt) refers to a compound formed by the neutralization reaction between an acid and a base, described in KAGAKU DAIJITEN (Encyclopedia of Chemistry in English), vol. 1, compact edition, 39th impression (KYORITSU SHUPPAN CO., LTD., Jun. 15, 2006), p. 1014, and consists of a negative component of the acid and a positive component of the base. Preferably, the phosphate is water-soluble. The term "water-soluble" means that the compound has solubility of 1 g or more per 100 g of water at 0 to 25° C. The source of the phosphorus is more preferably phosphate. A silica composite prepared using the phosphate tends to have smaller corrosive effect on stainless steel than that of a silica composite prepared using phosphoric acid, even if these silica composites have the same phosphorus content.

Specific examples of the phosphoric acid include phosphoric acid and pyrophosphoric acid. Specific examples of the phosphate include: ammonium phosphates such as ammonium phosphate, diammonium hydrogen phosphate, ammonium dihydrogen phosphate, and sodium ammonium hydrogen phosphate; and potassium hydrogen phosphate, aluminum hydrogen phosphate, sodium phosphate, and potassium phosphate. The phosphorus source is preferably ammonium phosphate which has relatively high solubility in water, more preferably at least one phosphate selected from the group consisting of ammonium phosphate, diammonium hydrogen phosphate, and ammonium dihydrogen phosphate. These phosphorus sources may be used alone or in combination of two or more thereof.

Preferably, the silica composite of the present embodiment, when used as a catalyst in fluidized-bed reaction, is in the form of spherical particles having an average particle size of 20 to 300 μm. The average particle size of the silica composite is more preferably 30 to 100 μm, further preferably 40 to 80 μm. Furthermore, a silica composite having a particle size distribution so that the particle sizes of 60% or more of all particles fall within the range of 2 times to 0.2 times the average particle size is preferable from the viewpoint of flowability. More preferably, the silica composite has higher sphericity in its shape. Its particles preferably have smooth surface. In this context, the average particle size and the particle size distribution can be determined using a laser diffraction/scattering particle size distribution analyzer (manufactured by Microtrac Inc., trade name "MT3000").

Moreover, high attrition resistance is preferable for the catalyst use from the viewpoint of a few losses of the silica composite during propylene production reaction. The attrition resistance of the silica composite can be determined based on attrition loss described later in Examples. Smaller attrition loss is preferable, and its measured value according to a method described in Examples is more preferably 1% by mass or less. The silica composite having high attrition resistance has a densely packed structure in its particles (solid spheres) and as such, tends to have a high bulk density. The bulk density of the silica composite is preferably 0.8 to 1.1 g/cc.

[Method for Producing Silica Composite]

The method for producing a silica composite according to the present embodiment is a method for producing a silica composite comprising the steps of:

(a) preparing a raw material mixture containing silica and zeolite;

(b) drying the raw material mixture to obtain a dried product; and (c) calcining the dried product, Wherein the method comprising the step of allowing the raw material mixture to contain phosphoric acid and/or phosphate or bringing a solution of phosphoric acid and/or phosphate into contact with the zeolite and/or the dried product, or a combination thereof to thereby adjust a phosphorus content in the silica composite to 0.01 to 1.0% by mass based on the total mass of the silica composite.

In the method for producing a silica composite according to the present embodiment, the phosphorus source may be supported in advance by the zeolite or added to the raw material mixture. Alternatively, the phosphorus source may be supported by the dried product. Also, a combination of these steps may be used.

Preferably, the method further comprises the step of bringing the calcined product obtained in the step (c) into contact with an acidic liquid (step (d)).

[Step (a): Step of Preparing Raw Material Mixture]

The step (a) is the step of preparing a raw material mixture containing silica and zeolite. The raw material mixture is prepared by mixing a silica source of a support with zeolite.

Preferably, the amount of each component added is adjusted so that the silica composite contains 15 to 65% by mass of the zeolite and 35 to 85% by mass of the silica.

Preferably, zeolite in an agglomerated form (form in which some of primary zeolite particles of approximately 0.05 to 2 μm are put together to form an agglomerate of approximately 5 to 20 μm) is used after being deagglomerated into approximately 0.05 to 3 μm by mechanical or chemical treatment. The method for deagglomeration is particularly preferably dry pulverization using a pulverizer such as a jet mill because of being convenient. Use of such zeolite in an agglomerated form after being deagglomerated tends to improve the surface smoothness and attrition resistance of the silica composite particles.

A cation of the zeolite is not particularly limited and may be $NH_4^+$ or $H^+$. Also, the zeolite may be in a form containing other elements (e.g., alkaline earth metals such as Mg, Ca, Sr, and Ba; transition metals such as Ti, Zr, V, Nb, Cr, Mo, W, Mn, Fe, Co, Ni, Cu, Ag, Au, Y, La, and Ce; and other elements such as Zn, B, Ga, Sn, and Sb).

For the production method of the present embodiment, it is also preferred to bring a solution of phosphoric acid and/or phosphate into contact with zeolite before mixing of the zeolite with the silica source to allow the phosphorus source no be supported by the zeolite. For this approach, it is preferred to adjust the amount of the solution of phosphoric acid and/or phosphate so that the zeolite maintains its powdery state.

A so-called impregnation method involves adding zeolite to a phosphorus source-containing solution to temporarily form slurry, which is then heated to remove the solvent, thereby allowing the phosphorus source to be supported by the zeolite. This method requires a solvent evaporation step and is thus complicated. In addition, the zeolite after solvent evaporation adheres to the inner surface of an apparatus and as such, is not suitable for industrial continuous production. An alternative method for allowing the phosphorus source to be supported by the zeolite involves bringing the zeolite into contact with the phosphorus source-containing solution while adjusting the amount of the phosphorus source-containing solution so that the zeolite maintains its powdery state, i.e., the zeolite does not form slurry. This method eliminates the need for evaporating the solvent and makes industrial continuous production exceedingly easy owing to the absence of zeolite adhesion to an apparatus. The silica composite obtained by allowing the phosphorus source to be supported by the zeolite so that the zeolite maintains its powdery state tends to have smaller corrosive effect than that of a silica composite obtained by forming zeolite slurry.

Specifically, the phosphorus source-containing solution (hereinafter, also referred to as a "phosphorus solution"; in this context, the term "solution" does not necessarily mean that phosphorus is in a completely dissolved state) is added in the range of 0.2 to 0.5 (mass ratio) to the zeolite. More preferably, the phosphorus solution is added at a 0.2 to 0.4 mass ratio to a zeolite powder. Water is preferable as a solvent for the phosphorus source. The method for addition preferably involves fluidizing the zeolite using a mixer, a blender, a kneader, or the like, and uniformly spraying the phosphorus solution over the fluidized zeolite. The temperature is preferably 5 to 95° C. Preferably, the phosphorus solution and the zeolite are mixed using a time and stirring intensity sufficient for compatibilizing them and usually mixed for 0.5 to 48 hours.

Preferably, the silica composite having a corrosion index of 10000 or lower is produced by preparing an aqueous solution containing 0.3 to 25% by mass of, for example, ammonium phosphate, adopted as the phosphorus source and allowing the ammonium phosphate to be supported in an amount that satisfies 0.1 to 10 g based on 100 g of the zeolite. For setting the corrosion index to 8000 or lower, it is preferred to allow the ammonium phosphate to be supported in an amount that satisfies 0.1 to 5.0 g based on 100 g of the zeolite.

A silica composite obtained using phosphoric acid as the phosphorus source tends to have a higher corrosion index than that of a silica composite obtained using phosphate such as ammonium phosphate, even if these silica composites have the same phosphorus content derived from the phosphoric acid or the ammonium phosphate. Accordingly, the phosphoric acid, when used as the phosphorus source, is preferably supported in an amount that satisfies 0.1 to 2.0 g based on 100 g of the zeolite.

Preferably, the zeolite thus obtained is calcined at 400 to 600° C. The calcined zeolite is prone to agglomerate. Thus, it is preferred to deagglomerate such agglomerated zeolite into approximately 0.05 to 3 μm. The method for deagglomeration is preferably dry pulverization using a pulverizer such as a hammer mill because of being convenient. A silica composite obtained by drying and calcining a raw material mixture prepared using agglomerated zeolite may have insufficient mechanical strength or attrition resistance. The agglomerated zeolite can be subjected to the subsequent step, after being pulverized, to thereby easily obtain a silica composite having sufficient mechanical strength and attrition resistance.

For example, colloidal silica, water glass (sodium silicate), or fumed silica can be used as the silica source for the support. The colloidal silica is preferably used because water glass has a large amount of Na which becomes a catalyst poison; and fumed silica is difficult to handle due to its low bulk density. Among others, $NH_4$-stabilized colloidal silica having a smaller amount of Na is particularly preferably used.

Preferably, the colloidal silica used as the silica source has a small silica particle size, more preferably a particle size of 4 to 20 nm, further preferably 4 to 15 nm. Use of such colloidal silica having a small particle size tends to improve the attrition resistance of the resulting silica composite. In this context, the silica particle size can be determined using a dynamic laser light scattering particle size distribution analyzer (manufactured by NIKKISO CO., LTD., trade name "Nanotrac UPA").

For the colloidal silica selected as the silica source, it is preferred to allow the raw material mixture to contain at least one water-soluble compound selected from the group consisting of nitrate, acetate, carbonate, sulfate, and chloride. In this context, the term "water-soluble compound" refers to a compound having solubility of 1 g or more in 100 g of water at 25° C. The water-soluble compound is preferably nitrate and also preferably respective ammonium salts of these water-soluble compounds, more preferably ammonium nitrate. Some of these water-soluble compounds may be used in combination. A silica composite obtained using the raw material mixture containing the water-soluble compound(s) tends to be excellent in attrition resistance and has a dense structure with a few internal voids. Such a silica composite is preferable for catalyst use in fluidized-bed reaction (hereinafter, the at least one water-soluble compound selected from the group consisting of nitrate, acetate, carbonate, sulfate, and chloride is also collectively referred to as a "processing aid").

The amount of the processing aid added is preferably in the range of 0.01 to 5.0, more preferably 0.03 to 3.0, further preferably 0.05 to 2.0, still further preferably 0.1 to 1.0, particularly preferably 0.25 to 0.5, in terms of mass ratio to silica contained in the colloidal silica (processing aid/silica). Silica composite particles obtained using the processing aid at a mass ratio less than 0.01 tend to hardly form a dense structure. On the other hand, a raw material mixture containing the processing aid at a mass ratio exceeding 5.0 is prone to be poorly dryable in the drying step.

Preferably, the raw material mixture containing the processing aid is made acidic with a mineral acid (nitric acid, hydrochloric acid, sulfuric acid, etc.), more preferably nitric acid, for preventing the colloidal silica from becoming unstable (gelated).

The pH of the raw material mixture supplemented with the mineral acid is preferably 0.01 to 3.0, more preferably 0.1 to 2.0, further preferably 0.5 to 1.5. A silica composite having higher attrition resistance can be obtained easily by preventing the gelation of the colloidal silica and drying the stating mixture with the sol state maintained. Such a silica composite is preferable for catalyst use in fluidized-bed reaction.

Preferably, the solids concentration of the raw material mixture is adjusted to 20 to 50% by mass. A silica composite obtained using a raw material mixture having a solids concentration lower than 20% by mass tends to have low attrition resistance for catalyst use in fluidized-bed reaction. On the other hand, a silica composite obtained using a raw material mixture having a solids concentration exceeding 50% by mass tends to be slightly inferior in particle surface smoothness.

The order in which the components contained in the raw material mixture are added is not particularly limited. Preferably, phosphorus-containing or -free zeolite is added to the silica source while it is stirred. Then, the mineral acid, the processing aid, and the like are added thereto as appropriate. In the case of the phosphorus-free zeolite, the desired amount of the phosphorus source can be added to this raw material mixture.

The raw material mixture thus prepared is stirred using a time and stirring intensity sufficient for mixing the components. The stirring time is usually 0.1 to 48 hours, and the temperature is usually 5 to 95° C.

For the production method of the present embodiment, it is not essential that the raw material mixture contains a phosphorus source. Specifically, the raw material mixture is not necessarily required to contain a phosphorus source when the phosphorus source is supported by the dried product as described later.

[Step (b): Drying Step]

The step (b) is the step of drying the raw material mixture to obtain a dried product. When phosphorus-containing zeolite is used or the phosphorus source is added to the raw material mixture, these components are also contained in the dried product.

The method for drying is not particularly limited. For example, for a silica composite for catalyst use in fluidized-bed reaction, it is preferred to dry the raw material mixture using a spray dryer. The raw material mixture can be sprayed by a method using, for example, a rotary disc, a two-fluid nozzle, a pressurized two-fluid nozzle, or a high-pressure nozzle. The microdroplets of the sprayed raw material mixture are dried by co-current or countercurrent contact with a heated gas in a drying room. The temperature at the gas inlet is preferably 100 to 400° C., more preferably 150 to 300° C. The temperature at the gas outlet is preferably 80 to 200° C., more preferably 90 to 150° C. Other conditions can be selected appropriately so that catalyst adhesion to the drying room can be minimized and spray drying can be performed stably for a long time to obtain the desired composite particles.

For a silica composite for catalyst use in fixed-bed reaction, it is preferred to granulate the raw material mixture into the desired shape, which is then dried using a furnace. The method for granulation is preferably extrusion, compression molding, rolling granulation, or fluidized-bed granulation. The drying temperature is preferably 100 to 400° C., and the drying time is preferably 0.5 to 100 hours.

The selected method or conditions for drying are not a determinant of the silica composite's corrosion index of 10000 or lower. Thus, any method or conditions for drying can be used without problems as long as the type or amount of the phosphorus source is appropriately set in the other steps. However, a silica composite obtained by adopting spray drying as the drying method tends to have a smaller corrosion index than that of a silica composite obtained by other drying methods, even if the same raw materials are used. A microparticle containing zeolite and silica obtained by spray drying tends to have a lower phosphorus concentration on the surface than in the particle. Such a particle having a lower phosphorus concentration on the surface than in the particle tends to have smaller corrosive effect than a particle having the same phosphorus concentration and uniform phosphorus distribution throughout the particle.

In the production method of the present embodiment, the solution of phosphoric acid and/or phosphate may be brought into contact with the dried product obtained by the step (b) to thereby allow the phosphorus source to be supported thereby. As described above, the phosphorus source may be supported in advance by the zeolite or added to the raw material mixture in the method for allowing the silica composite to contain the phosphorus. However, a silica composite obtained by allowing the phosphorus source to be supported by the dried product obtained in the step (b) tends to cause much less corrosion of stainless steel in a high-temperature steam atmosphere. Thus, in a preferable aspect, the dried product obtained through the steps (a) and (b) is free from the phosphorus source, which is then supported by the dried product. Two or more of these approaches (i.e., the phosphorus source is supported in advance by the zeolite, added to the raw material mixture, or supported by the dried product) may be used in combination.

Preferably, the phosphorus source is supported by the dried product by, not particularly limited to, a method which involves bringing the dried product into contact with a phosphorus source-containing solution while adjusting the amount of the phosphorus source-containing solution so that the dried product maintains its powdery state, as in the case of allowing it to be supported by the zeolite. This makes a catalyst production process simple and industrial continuous production exceedingly easy, as in the description above. A silica composite produced with the powdery state maintained tends to have much smaller corrosive effect than that of a silica composite produced by forming slurry.

Specifically, the phosphorus source-containing solution is added in the range of 0.2 to 0.5 (mass ratio) to the dried product. More preferably, the phosphorus solution is added thereto at a 0.2 to 0.4 mass ratio. Water is preferable as a solvent in the phosphorus source-containing solution. The method for addition preferably involves fluidizing the dried product using a mixer, a blender, a kneader, or the like, and uniformly spraying the solution over the dried product. In this case, the temperature is preferably 10 to 95° C. Preferably, the solution and the dried product are further mixed using a time and stirring intensity sufficient for compatibilizing them and usually mixed for 0.5 to 48 hours.

Preferably, the silica composite having a corrosion index of 10000 or lower is prepared by preparing an aqueous solution containing 0.1 to 15% by mass of, for example, ammonium phosphate, adopted as the phosphorus source added to the dry product and adjusting the amount of the ammonium phosphate to 0.05 to 5.0 g based on 100 g of the dried product. For setting the corrosion index to 8000 or lower, it is preferred to adjust the amount of the ammonium phosphate to 0.05 to 2.5 g based on 100 g of the dried product.

A silica composite obtained using phosphoric acid as the phosphorus source tends to have a higher corrosion index than that of a silica composite obtained using phosphate such as ammonium phosphate, even if these silica composites have the same phosphorus content derived from the phosphoric acid or the ammonium phosphate. Accordingly, the amount of the phosphoric acid adopted as the phosphorus source is preferably adjusted to 0.05 to 2.0 g based on 100 g of the dried product.

[Step (c): Calcination Step]

The step (c) is the step of calcining the dried product obtained in the step (b). The dried product is calcined to obtain a calcined product.

The calcination of the dried product can be performed using, not particularly limited to, a muffle furnace, a rotary furnace, a tunnel furnace, a tubular furnace, a fluidized-bed calciner, a kiln, or the like. A continuous-feed rotary kiln is industrially preferably used for the calcination. The calcination temperature is preferably 400 to 1000° C., more preferably 500 to 850° C., from the viewpoint of improving the attrition resistance of the resulting silica composite particles. The calcination time is preferably 0.1 to 48 hours, more preferably 0.5 to 10 hours. For example, air, steam, nitrogen, or helium can be selected as a calcination atmosphere. The calcination may be performed under pressure or reduced pressure. Also, the calcination may be performed repetitively.

The calcination step promotes the formation of a phosphorus compound from the phosphorus source and improvement in the attrition resistance of the silica composite particles by the sintering of silica contained in the support.

[Step (d): Acid Washing Step]

The step (d) is the step of bringing the calcined product obtained in the calcination step (c) into contact with an acidic liquid. In the step (d), redundant phosphorus components can be removed from the calcined product obtained in the step (c), and alkali metal components, etc., derived from the silica source can also be removed. A silica composite obtained through this step can have much smaller corrosive effect on stainless steel.

Conditions for the step (d) are not particularly limited and preferably involve bringing the calcined product into contact with an aqueous solution containing, for example, 0.1 to 3 M mineral acid (nitric acid, sulfuric acid, hydrochloric acid, etc.) at a temperature of 10 to 95° C. for 0.1 to 48 hours. This treatment may be repeated several times as appropriate.

The acid washing step is not essential for obtaining the silica composite having a corrosion index of 10000 or lower. The silica composite having a corrosion index of 10000 or lower may be obtained even without acid washing as long as the type of the phosphorus source, the amount of the phosphorus source added, or the like is appropriately set. However, in such a case as well, the corrosion index can be adjusted to a much more preferable value by performing acid washing.

On the other hand, a silica composite having a corrosion index exceeding 10000 may be acid-washed to thereby adjust its corrosion index to 10000 or lower. In this case, the acid washing is preferably performed using 0.1 to 1 M aqueous nitric acid solution under conditions involving 5 to 50° C., 0.5 to 10 hours, and a solids concentration of 5 to 25% by mass. For setting the corrosion index to 8000 or lower, it is preferred to perform the acid washing using 0.1 to 1 M aqueous nitric acid solution under conditions involving 15 to 50° C., 1 to 10 hours, and a solids concentration of 5 to 10% by mass.

The silica composite thus acid-washed is filtered, washed with water, and dried, and may be calcined again at 400 to 800° C. as appropriate.

Preferably, the silica composite produced as described above is also treated with steam. The steaming treatment can be carried out by a general method. For example, the silica composite is brought into contact with a gas containing 10 to 90% by volume of steam (balance: usually, air) at a temperature of 500 to 1000° C. for 0.1 to 100 hours. The steaming treatment tends to inhibit coking during the reaction and improve propylene yields.

[Method for Producing Propylene]

Next, a method for producing propylene will be described which comprises the step of bringing a silica composite obtained by the production method of the present embodiment into contact with a hydrocarbon source containing at least one component selected from the group consisting of ethylene, ethanol, methanol, and dimethyl ether in the presence of steam.

The ethylene concentration in the hydrocarbon source (except for the coexisting steam) is preferably 40 to 100% by mass, more preferably 50 to 80% by mass, further preferably 50 to 70% by mass, from the viewpoint of reaction efficiency. Since the ethanol, methanol, or dimethyl ether used forms ethylene through dehydration reaction, this is also taken into consideration for calculating the ethylene concentration.

The production of propylene is performed in the presence of steam from the viewpoint of inhibiting deactivation attributed to coking during the reaction. The steam concentration is preferably 10 to 60% by mass, more preferably 20 to 40% by mass, based on the total mass of the raw material containing the hydrocarbon source and the steam.

The hydrocarbon source can contain, in addition to ethylene, ethanol, methanol, and/or dimethyl ether, alkanes such as methane, ethane, propane, butane, pentane, hexane, heptane, octane, and nonane; olefins such as propylene, butene, pentene, hexene, heptene, octene, and nonene; aromatic compounds such as benzene, toluene, and xylene; dienes such as butadiene, pentadiene, cyclopentadiene, and cyclohexadiene; and acetylenes such as acetylene and methylacetylene. The hydrocarbon source can also contain oxygen-containing compounds such as propanol, t-butyl alcohol, methyl t-butyl ether, and diethyl ether. The hydrocarbon source may additionally contain hydrogen sulfide, hydrogen, nitrogen, carbon dioxide, carbon monoxide, etc.

The reaction is preferably performed by a fluidized-bed method using a fluidized-bed reactor. The reaction temperature is preferably in the range of 300 to 650° C., more preferably 400 to 600° C. The reaction pressure is preferably in the range of −0.05 to 1.0 MPa (gage pressure), more preferably 0 (atmospheric pressure) to 0.5 MPa (gage pressure).

The feed rate of the hydrocarbon source is preferably 0.01 to 10 hr$^{-1}$, more preferably 0.1 to 5.0 hr$^{-1}$, further preferably 0.1 to 1.0 hr$^{-1}$, in terms of weight hourly space velocity (WHSV) based on the silica composite. In this context, WHSV can be calculated based on the amount of ethylene supplied (kg/h)/the amount of the silica composite (kg). Since the ethanol, methanol, or dimethyl ether used forms ethylene through dehydration reaction, this is also taken into consideration for calculating the amount of ethylene supplied.

Preferably, the silica composite used in the reaction is calcined at 400 to 700° C. in an oxygen-containing atmosphere to remove coke accumulating during the reaction. The process of removing coke by combustion is also called "regeneration process". For fixed-bed reaction, it is preferred to prepare a plurality of reactors and alternately perform reaction and regeneration at the given time intervals. For fluidized-bed reaction, it is preferred to introduce a portion or the whole of the silica composite used in the reaction into a regenerator in which the introduced silica composite is regenerated and then returned to the reactor for reaction.

The reaction product containing the formed propylene may be recycled to the reactor, together with unreacted ethylene or some high-boiling components such as butene, after being separated from the objective compound (propylene) by distillation or the like.

The production of propylene from ethylene and/or ethanol exhibits the maximum propylene yield at an ethylene conversion rate around 70% because of its equilibrium reaction. Thus, the reaction is preferably performed at an ethylene conversion rate in the range of 45 to 85%, more preferably 50 to 80%, for efficiently obtaining propylene.

EXAMPLES

Hereinafter, the present embodiment will be described in more detail with reference to Examples. However, the present embodiment is not limited to Examples below.

[Methods for Determining Various Physical Properties]

Various physical properties were determined by the following methods.

(1) Structure Type of Zeolite

The structure type was identified by measuring the X-ray diffraction pattern of the zeolite using a powder X-ray diffractometer (manufactured by Rigaku Corp., trade name "RINT") and comparing it with the diffraction patterns of zeolites known in the art. The measurement conditions were set to a Cu cathode, tube voltage: 40 kV, tube current: 30 mA, and scanning speed: 1 deg/min.

(2) $SiO_2/Al_2O_3$ Ratio (by Mol) of Zeolite

The zeolite was completely dissolved in a sodium hydroxide solution to prepare a sample solution. The amounts of Si and Al contained in the sample solution were measured by a routine method using an ICP (inductively coupled plasma) emission spectrometer (manufactured by Rigaku Corp., trade name "JY138"). The $SiO_2/Al_2O_3$ ratio (by mol) was calculated from the results. The measurement conditions were set to radio frequency power: 1 kW, plasma gas: 13 L/min, sheath gas: 0.15 L/min, nebulizer gas: 0.25 L/min, Si measurement wavelength: 251.60 nm, and Al measurement wavelength: 396.152 nm.

(3) Phosphorus Content in Silica Composite

The phosphorus content in a silica composite was determined by a routine method using an X-ray fluorescence analyzer (manufactured by Rigaku Corp., trade name "RIX3000"). The measurement conditions were set to tube voltage: 50 kV and tube current: 50 mA with P-Kα rays. The contents of the other components in the composition of the silica composite were calculated from the amounts of the components added.

(4) Solid-State $^{31}$P-NMR Measurement of Silica Composite

The form of phosphorus in a silica composite was determined by solid-state $^{31}$P-NMR (manufactured by Bruker, trade name "Biospin DSX400"). The measurement conditions were set to probe: 4BLX-1H, frequency: 161.98 MHz, observation width: 451 ppm, pulse width: 45° C., 512 runs in total, and chemical shift (0 ppm) reference: 85% aqueous phosphoric acid solution.

(5) Electron Microscopic Image of Silica Composite

The electron microscopic image of a silica composite was obtained by a routine method using an electron microscope (manufactured by Hitachi, Ltd., trade name "S-800").

(6) Bulk Density of Silica Composite

The bulk density of a silica composite was measured by a routine method using a bulk specific gravity meter (manufactured by TSUTSUI SCIENTIFIC INSTRUMENTS CO., LTD., model "Z-2504").

(7) Attrition Loss Determination of Silica Composite Particles

The attrition loss serving as an index for the mechanical strength of silica composite particles was determined using a jet flow apparatus. The jet flow apparatus used had a gas inlet with three 0.4 mm orifices and was provided with a powder elevation part having an inside diameter of 35 mm and a length of 700 mm, a powder separation part having an inside diameter of 110 mm and a length of 600 mm, and a fine powder capturing part. 52.5 g of a silica composite containing 2.5 g of water was loaded into the jet flow apparatus at room temperature. Then, air containing water in an amount corresponding to vapor pressure was circulated at 5.8 NL/min from the gas inlet. The mass of fine silica composite powders collected into the fine powder capturing part was measured from 0 to 5 hours and 5 to 20 hours into measurement. The attrition loss was determined according to the following equation:

Attrition loss (% by mass)=$A/(B-C)\times 100$

In this context, A represents the mass (g) of the fine silica composite powders collected from 5 to 20 hours into measurement; C represents the mass (g) of the fine silica composite powders collected from 0 to 5 hours into measurement; and B represents the total mass (g) of the silica composite subjected to the test.

(8) Determination of Corrosion Index in High-Temperature Steam Atmosphere

A silica composite was compacted using a compression molding machine and then crushed into 6- to 16-mesh particles. 12 g of the particles was loaded, together with a stainless s-eel (SUS304) specimen (20 mm×10 mm, thickness: 1 mm), into a quartz reaction tube. The specimen was kept at 550° C. for 7 days in the reaction tube with gasses (consisting of 80 vol % steam and 20 vol % nitrogen) circulated. The resulting specimen after the test was observed under a microscope, and the corrosion index was determined according to the following equation:

Corrosion index=the number of corrosion pits (pits/cm$^2$)×average size of corrosion pits (μm)×average depth of corrosion (μm)

In this context, the number of corrosion pits was determined by counting the number of pits formed by corrosion per cm$^2$ of a specimen. The average size of corrosion pits was determined by measuring the size of pits formed by corrosion and determining the arithmetic mean thereof. The average depth of corrosion was determined by cutting a specimen, measuring the depth of pits formed by corrosion in the obtained cross section, and determining the arithmetic mean thereof.

(9) Method for Producing Propylene

Silica composites obtained in Examples and Comparative Examples below were treated with steam under conditions involving 650° C., 24 hours, a steam partial pressure of 0.8 atmospheres, and a nitrogen gas partial pressure of 0.2 atmospheres. 25.7 g of each silica composite was loaded into a stainless fluidized-bed reactor having an inside diameter of 1 inch. Then, ethylene at 9.9 g/hr, hydrogen at 0.7 g/hr, water at 4.9 g/hr, and nitrogen at 5.3 g/hr were circulated in the reactor, while reaction was performed at a reaction temperature of 550° C., a reaction pressure of 0.14 MPa (gage pressure), and a WHSV of 0.4 hr$^{-1}$ (based on the silica composite).

However, the amount of a silica composite containing zeolite having a SiO$_2$/Al$_2$O$_3$ ratio (by mol) of 200 or more was appropriately adjusted within the WHSV range of 0.1 to 0.4 hr$^{-1}$. The resulting reaction products were analyzed by gas chromatography using an apparatus (manufactured by Shimadzu Corp., GC-17A, TCD-FID serial linkage model) directly linked to the reactor.

Ethylene conversion rates and propylene yields were calculated according to the following equations:

Ethylene conversion rate=(Ethylene concentration in supplied flow at the inlet of the reactor−Ethylene concentration in supplied flow at the outlet of the reactor)/Ethylene concentration in supplied flow at the inlet of the reactor×100 (a)

Propylene yield=Mass of propylene formed by the reaction/Mass of ethylene supplied to the reactor×100 (b)

Since ethanol, methanol, or dimethyl ether used as a raw material forms ethylene through dehydration reaction, this was taken into consideration for calculating propylene yields based on the mass of ethylene. The yield of formed water was not used in the calculation of propylene yields.

The ethanol conversion rate was calculated according to the following equation:

Ethanol conversion rate=(Ethanol concentration in supplied flow at the inlet of the reactor−Ethanol concentration in supplied flow at the outlet of the reactor)/Ethanol concentration in supplied flow at the inlet of the reactor×100 (c)

The methanol conversion rate was calculated according to the following equation:

Methanol conversion rate=(Methanol concentration in supplied flow at the inlet of the reactor−Methanol concentration in supplied flow at the outlet of the reactor)/Methanol concentration in supplied flow at the inlet of the reactor×100 (d)

The dimethyl ether conversion rate was calculated according to the following equation:

Dimethyl ether conversion rate=(Dimethyl ether concentration in supplied flow at the inlet of the reactor−Dimethyl ether concentration in supplied flow at the outlet of the reactor)/Dimethyl ether concentration in supplied flow at the inlet of the reactor×100 (e)

[Method for Preparing Zeolite]

Zeolite used in Examples 1, 10, 17, 18 and 25 and Comparative Examples 1 to 4 was synthesized as follows: first, zeolite was hydrothermally synthesized in the same way as in Example 3 of Japanese Patent Publication No. 2-44771 (Japanese Patent Laid-Open No. 59-54620) except that wet cake of uniform compound D was prepared so that the zeolite had a SiO$_2$/Al$_2$O$_3$ ratio (by mol) of 27.

The obtained zeolite was sufficiently washed with water and dried at 120° C. For converting the cation type of the zeolite to H$^+$, the zeolite was then ion-exchanged at 25° C. for 1 hour using 1 M aqueous nitric acid solution, further washed with water, and dried at 120° C.

The SiO$_2$/Al$_2$O$_3$ ratio (by mol) of the zeolite thus obtained was determined to be 27 according to the method described above. Its structure type was identified as MFI type (ZSM-5) according to the determination method described above. The identification of the structure type was made with reference to the description of Japanese Patent Publication No. 46-10064 (the same holds true for the description below, unless otherwise specified).

This zeolite was in the form of agglomerated primary particles and was thus pulverized (deagglomerated) into an average particle size of 3 μm using a jet mill (manufactured by Nippon Pneumatic MFG. Co., Ltd., model: "LJ").

Zeolite used in Examples 2 to 9, and 13 to 16 and Comparative Example 5 was synthesized as follows: first, the amount of aluminum sulfate.x hydrate (manufactured by Wako Pure Chemical Industries, Ltd., special-grade reagent) contained in a solution A and the amount of water glass (manufactured by Fuji Kagaku Corp., trade name "No. 3 Sodium Silicate", 29.0% by mass of SiO$_2$, 9.5% by mass of Na$_2$O, balance: water) contained in a solution B were determined so that the zeolite had a SiO$_2$/Al$_2$O$_3$ ratio (by mol) of 480 (Example 2), 50 (Example 3 and Comparative Example 5), 156 (Example 4), 210 (Example 5), 280 (Example 6), or 240 (Examples 7 to 9 and 13 to 16). Subsequently, the determined amounts of the solutions A and B were mixed at 5000 rpm for 30 minutes using a homogenizer. Furthermore, hydrothermal synthesis was conducted at 160° C. for 3 days (stirring speed: 600 rpm). Zeolite was hydrothermally synthesized in the same way as in Example 2 of Japanese Patent Publication No. 61-21985 (Japanese Patent Laid-Open No. 50-5335) except for the procedures described above.

The obtained zeolite was sufficiently washed with water, dried at 120° C., and then calcined at 550° C. for 3 hours in an air atmosphere in an electric furnace. For converting the cation type of the calcined zeolite to $NH_4^+$, the zeolite was then ion-exchanged at 25° C. for 1 hour using 1M aqueous ammonium chloride solution, further washed with water, and dried at 120° C.

The $SiO_2/Al_2O_3$ ratios (by mol) of the obtained zeolites were determined as described above according to the method described above. The structure types were all identified as MFI type (ZSM-5) according to the determination method described above.

Zeolite used in Example 12 was synthesized as follows: 970 g of colloidal silica (manufactured by NISSAN CHEMICAL INDUSTRIES, LTD., trade name "SNOWTEX 30", silica content: 31% by mass), 2240 g of an aqueous solution containing 10% by mass of tetra-n-ammonium hydroxide (Wako Pure Chemical Industries, Ltd., special-grade reagent), 600 g of ethanol (Wako Pure Chemical Industries, Ltd., special-grade reagent), and 3.06 g of aluminum sulfate.tetradeca- to octadecahydrates (Wako Pure Chemical Industries, Ltd., special-grade reagent) were mixed at 5000 rpm for 30 minutes using a homogenizer to obtain a solution. The solution was subjected to hydrothermal synthesis in an autoclave at 160° C. for 190 hours (stirring speed: 600 rpm) to obtain zeolite. The obtained zeolite was washed with water, calcined, and $NH_4^+$-exchanged in the same way as above.

The $SiO_2/Al_2O_3$ ratio (by mol) of the obtained zeolite was determined to be 1000 according to the method described above. Its structure type was identified as MFI type (ZSM-5) according to the determination method described above.

Zeolite used in Example 11 was commercially available silicalite of MFI type (manufactured by Sud-Chemie Catalysts Japan, Inc., trade name: TZP-9023). The $SiO_2/Al_2O_3$ ratio (by mol) of the zeolite was determined to be 10000 according to the method described above. Its structure type was identified as MFI type (ZSM-5) according to the determination method described above.

Example 1

A raw material mixture was prepared as follows (step (a)):
300 g of ZSM-5 ($SiO_2/Al_2O_3$ ratio (by mol)=27) was added to 2000 g of colloidal silica (manufactured by Nalco Company, trade name "Nalco 2326", silica particle size: 5 nm, silica content: 15% by mass, pH=9) while it was stirred. 40 g of an aqueous solution containing 61% by mass of nitric acid (manufactured by Wako Pure Chemical Industries, Ltd., special-grade reagent) was added thereto to adjust the pH to 1.0. Then, 100 g of ammonium nitrate (manufactured by Wako Pure Chemical Industries, Ltd., special-grade reagent) was added thereto as a processing aid. This raw material mixture was stirred at 25° C. for 2 hours.

The raw material mixture was spray-dried using a spray dryer (manufactured by OHKAWARA KAKOHKI Co., Ltd., model: "OC-16") to obtain a dried product (step (b)). The spraying was performed using a disc-type atomizer at hot-air inlet and outlet temperatures of 230° C. and 130° C., respectively.

Phosphate was supported by this dried product as follows:
31 g of diammonium hydrogen phosphate (manufactured by Wako Pure Chemical Industries, Ltd., special-grade reagent, solubility in 100 g of water: 131 g (15° C.)) was dissolved in pure water to prepare 266 g of an aqueous phosphate solution. 665 g of the dried product was loaded into a powder stirrer (manufactured by AICHI ELECTRIC CO., LTD., Rocking Mixer), and the aqueous phosphate solution was uniformly sprayed thereover at 25° C. with the powder fluidized. The dried product maintained its powdery state without forming slurry. This supporting method applies to phosphorus source supporting method A in Tables 1 to 3. In Examples below, all dried products obtained by this supporting method maintained their powdery states.

The obtained dried product with the phosphate supported thereby was calcined at 700° C. for 1 hour in an air atmosphere using a muffle furnace (step (c)).

Finally, this calcined product was added to 0.1M aqueous nitric acid solution to adjust the slurry concentration to 10% by mass, and the mixture was stirred at 25° C. for 1 hour (step (d)).

Then, the slurry was filtered, washed with water, and dried at 120° C. for 12 hours to obtain a silica composite.

Figure 8:
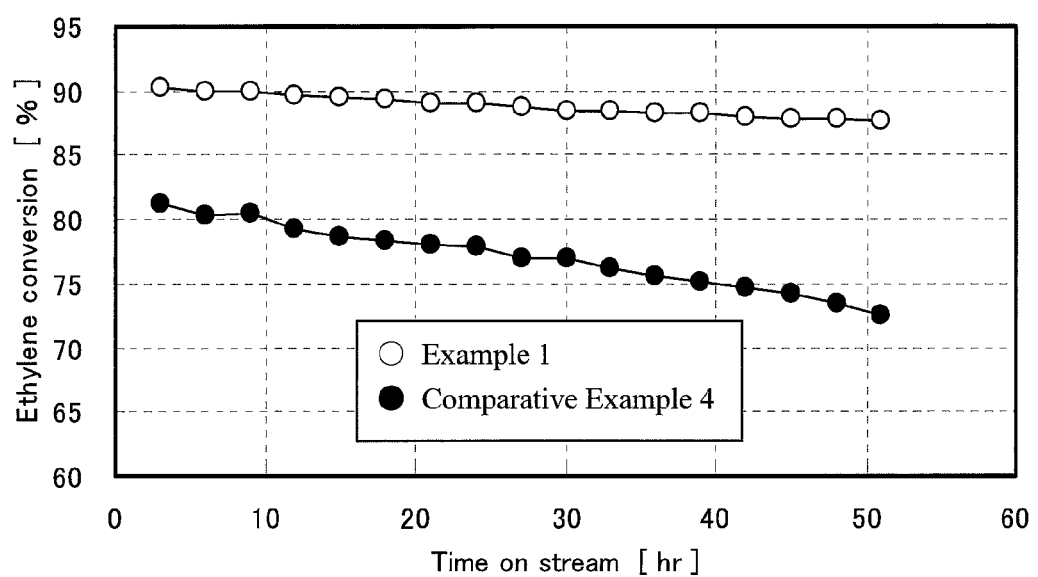
FIG. 8 shows time-dependent change in the ethylene conversion rate of fluidized-bed reaction using silica composites obtained in Example 1 and Comparative Example 4.

Analysis and reaction results of the obtained silica composite are shown in Table 1 and FIG. 8.

FIG. 1 shows an electron micrograph of the silica composite obtained in Example 1 (magnification: 150 times). As is evident from FIG. 1, the silica composite was in the form of spherical particles having smooth surface.

Figure 9:
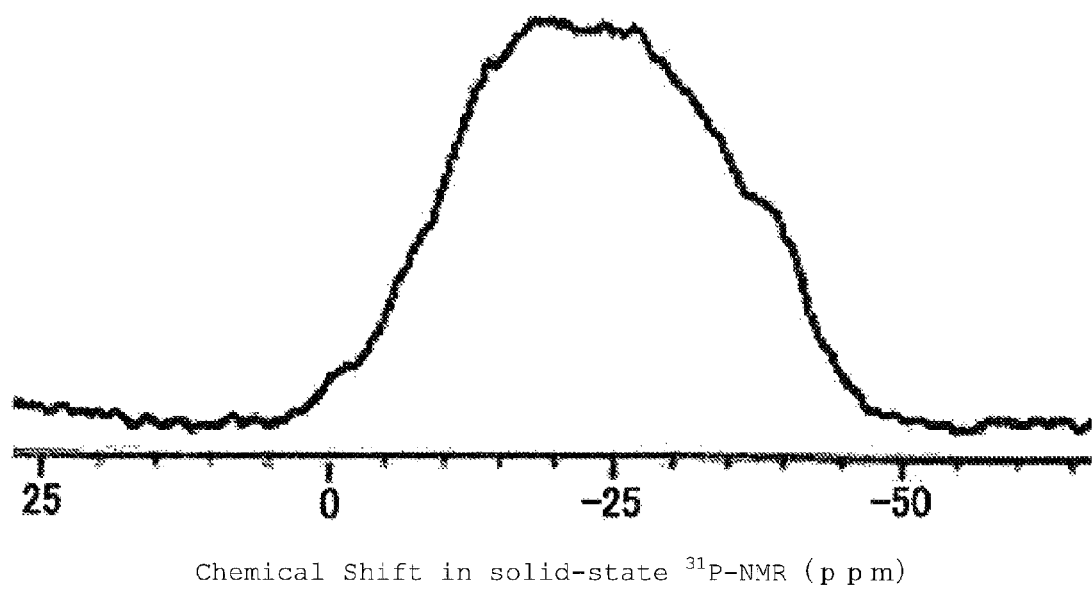
FIG. 9 shows a solid-state $^{31}$P-NMR spectrum of the silica composite of Example 1.

FIG. 9 shows the solid-state $^{31}$P-NMR signal of the silica composite obtained in Example 1. As is evident from FIG. 9, phosphorus compounds in this silica composite contained few phosphoric acids attributed to 0 ppm signal and were mostly phosphorus compounds other than the phosphoric acids attributed to −5 to −45 ppm signals.

Example 2

A silica composite was produced in the same way as in Example 1 except that: the colloidal silica was changed to 882 g of trade name "Nalco DVZSN006" manufactured by Nalco Company (silica particle size: 12 nm, silica content: 34% by mass, pH=9); the zeolite was changed to 300 g of ZSM-5 ($SiO_2/Al_2O_3$ ratio (by mol)=480); and the phosphorus source was changed to 3.1 g of diammonium hydrogen phosphate.

Analysis and reaction results of the obtained silica composite are shown in Table 1.

Figure 2:
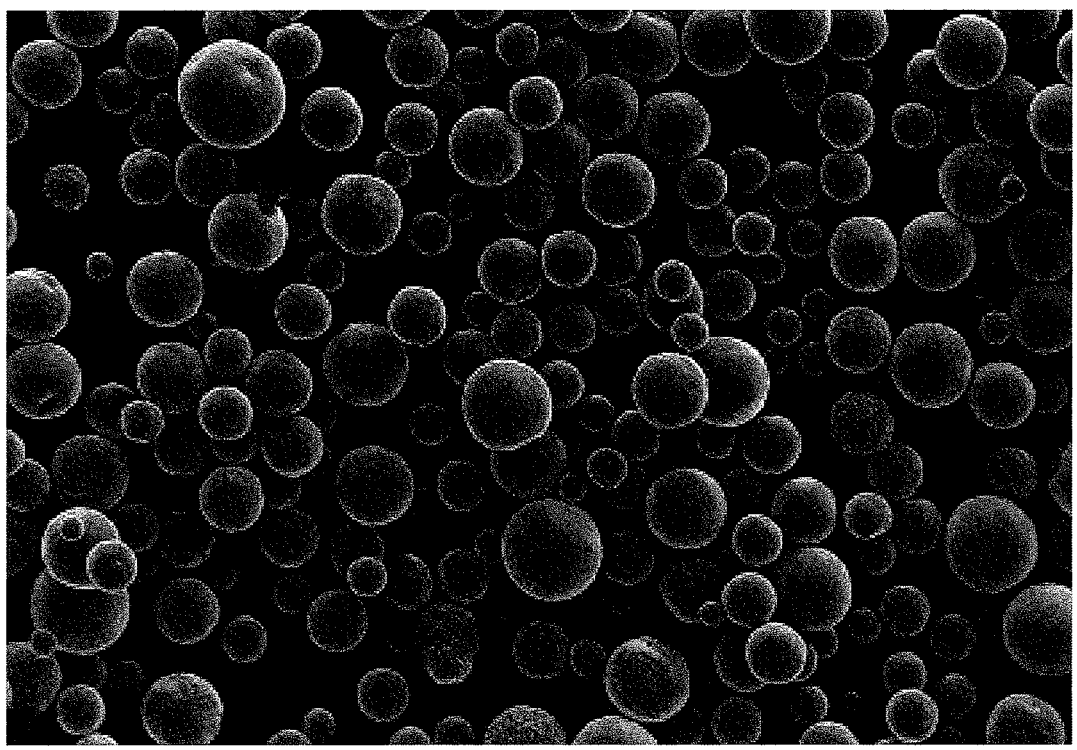
FIG. 2 shows an electron micrograph of a silica composite of Example 2 (magnification: 150 times).

FIG. 2 shows an electron micrograph of the silica composite obtained in Example 2 (magnification: 150 times). As is evident from FIG. 2, the silica composite was in the form of spherical particles having smooth surface.

Figure 5:
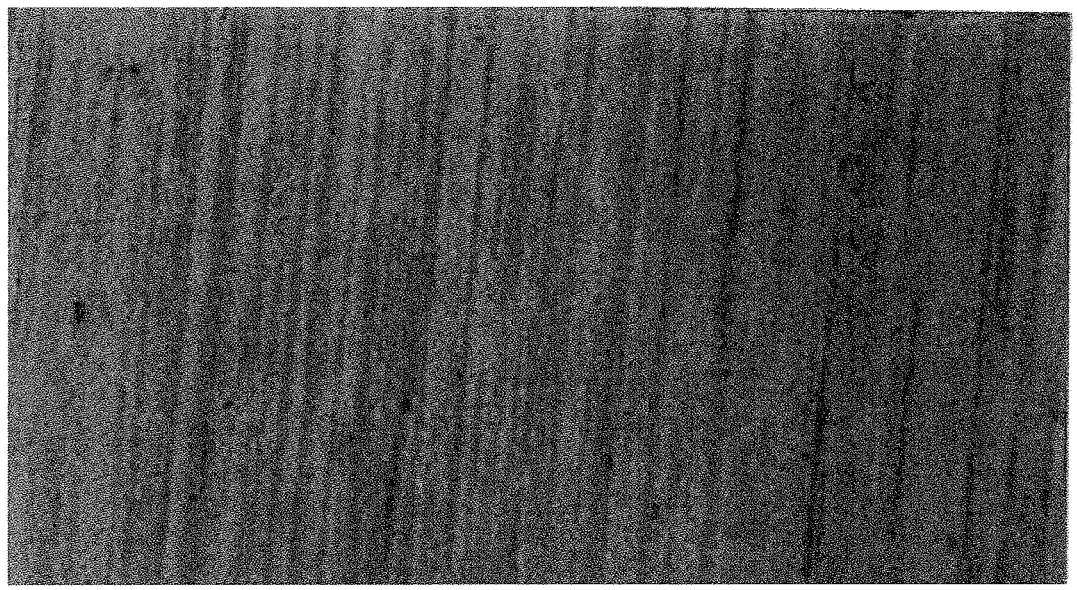
FIG. 5 shows a micrograph of a specimen after a corrosion test of Example 2 (magnification: 120 times).

FIG. 5 shows a micrograph of a SUS304 specimen after corrosion test using the silica composite of Example 2 (magnification: 120 times). As is evident from FIG. 5, the specimen after the test did not corrode.

Example 3

A silica composite was produced in the same way as in Example 1 except that: the zeolite was changed to 300 g of ZSM-5 ($SiO_2/Al_2O_3$ ratio (by mol)=50); and the phosphorus source was changed to 26.7 g of ammonium dihydrogen phosphate (manufactured by Wako Pure Chemical Industries, Ltd., special-grade reagent, solubility in 100 g of water: 22.7 g (0° C.)).

Analysis and reaction results of the obtained silica composite are shown in Table 1.

Example 4

A silica composite was produced in the same way as in Example 1 except that: the zeolite was changed to 300 g of ZSM-5 ($SiO_2/Al_2O_3$ ratio (by mol)=156); and the phosphorus source was changed to 7.0 g of ammonium phosphate (manufactured by Wako Pure Chemical Industries, Ltd., special-grade reagent, solubility in 100 g of water: 65 g (25° C.)).

Analysis and reaction results of the obtained silica composite are shown in Table 1.

Example 5

A silica composite was produced in the same way as in Example 1 except that: the zeolite was changed to 300 g of ZSM-5 ($SiO_2/Al_2O_3$ ratio (by mol)=210); and 133 g of an aqueous solution containing 7.6 g of sodium dihydrogen phosphate.dihydrate (solubility in 100 g of water: 91 g (0° C.)) dissolved in pure water was sprayed.

Analysis and reaction results of the obtained silica composite are shown in Table 1.

Example 6

A silica composite was produced in the same way as in Example 1 except that: the zeolite was changed to 300 g of ZSM-5 ($SiO_2/Al_2O_3$ ratio (by mol)=280); and the phosphorus source was changed to 3.0 g of potassium dihydrogen phosphate (solubility in 100 g of water: 14.8 g (0° C.)).

Analysis and reaction results of the obtained silica composite are shown in Table 1.

Example 7

A silica composite was produced in the same way as in Example 1 except that: the zeolite was changed to 300 g of ZSM-5 ($SiO_2/Al_2O_3$ ratio (by mol)=240); and the amount of diammonium hydrogen phosphate was changed to 9.0 g.

Analysis and reaction results of the obtained silica composite are shown in Table 1.

Example 8

300 g of ZSM-5 ($SiO_2/Al_2O_3$ ratio (by mol)=240) was added to 2000 g of colloidal silica (manufactured by Nalco Company, trade name "Nalco 2326", silica particle size: 5 nm, silica content: 15% by mass, pH=9) while it was stirred. Subsequently, 9.0 g of diammonium hydrogen phosphate was added thereto. 40 g of an aqueous solution containing 61% by mass of nitric acid was further added thereto to adjust the pH to 1.0. Then, 100 g of ammonium nitrate was added thereto as a processing aid. This raw material mixture was stirred at 25° C. for 2 hours.

Subsequently, spray drying, calcination, and acid washing were performed in the same way as in Example 1 to produce a silica composite except that the phosphate was not supported by the dried product. This supporting method applies to phosphorus source supporting method B in Tables 1 to 3.

Analysis and reaction results of the obtained silica composite are shown in Table 1.

Example 9

200 g of an aqueous solution containing 12.8 g of diammonium hydrogen phosphate was sprayed to 500 g of ZSM-5 ($SiO_2/Al_2O_3$ ratio (by mol)=240) while it was stirred using a mixing stirrer (manufactured by Dalton Corporation, model: Twin Mix). In this case, the zeolite maintained its powdery state without forming slurry. This supporting method applies to phosphorus source supporting method C in Table 1. In Examples below, all zeolites obtained by this supporting method maintained their powdery states.

Subsequently, the resulting zeolite was calcined at 600° C. for 1 hour. This calcined product was in an agglomerated form having an average particle size of approximately 15 µm and was thus pulverized into an average particle size of 3 µm or smaller using a hammer mill (manufactured by Dalton Corporation, model: AIIW-5).

A raw material mixture was prepared in the same way as in Example 1 using 300 g of the thus-pulverized ZSM-5 containing the phosphorus.

Subsequently, spray drying, calcination, and acid washing were performed in the same way as in Example 1 to produce a silica composite except that the phosphate was not supported by the dried product.

Analysis and reaction results of the obtained silica composite are shown in Table 1. The silica composite obtained in Example 9 was in the form of smooth particles spherical in shape, as in Examples 1 and 2.

Example 10

A silica composite was produced in the same way as in Example 1 except that: the colloidal silica was changed to 1430 g of trade name "Nalco 2326" manufactured by Nalco Company; 122 g of alumina sol (manufactured by NISSAN CHEMICAL INDUSTRIES, LTD., trade name "Alumina Sol-100", alumina content: 10% by mass) and 57 g of clay mineral kaolin (manufactured by Engelhard Corp., trade name "ASP-600") were added to the raw material mixture; and the amount of diammonium hydrogen phosphate supported by the dried product was changed to 12.6 g.

Analysis and reaction results of the obtained silica composite are shown in Table 2.

Example 11

A silica composite was produced in the same way as in Example 9 except that: the zeolite was changed to silicalite of MFI type ($SiO_2/Al_2O_3$ ratio (by mol)=10000); and the amount of diammonium hydrogen phosphate was changed to 0.7 g.

Analysis and reaction results of the obtained silica composite are shown in Table 2.

Example 12

A silica composite was produced in the same way as in Example 8 except that: the zeolite was changed to silicalite of MFI type ($SiO_2/Al_2O_3$ ratio (by mol)=1000); and the amount of diammonium hydrogen phosphate was changed to 1.3 g.

Analysis and reaction results of the obtained silica composite are shown in Table 2.

Example 13

A silica composite was produced in the same way as in Example 7 except that the diammonium hydrogen phosphate was changed to 5.8 g of phosphoric acid (manufactured by Wako Pure Chemical Industries, Ltd., special-grade reagent).

Analysis and reaction results of the obtained silica composite are shown in Table 2.

Example 14

In this example, diammonium hydrogen phosphate was supported by zeolite by the impregnation method.

500 g of an aqueous solution containing 12.8 g of diammonium hydrogen phosphate was added to 500 g of ZSM-5 ($SiO_2/Al_2O_3$ ratio (by mol)=240). The zeolite formed slurry without maintaining its powdery state. This slurry was transferred to a flask and dried under reduced pressure at 90° C. using an evaporator. This supporting method applies to phosphorus source supporting method C* in Table 2. This zeolite adhered to the inner surface of the flask and was thus laboriously collected. The collected zeolite was calcined at 600° C. for 1 hour. This calcined product was in an agglomerated form having an average particle size of 30 μm or larger.

A silica composite was produced in the same way as in Example 9 except that this phosphorus-containing ZSM-5 in an agglomerated form was directly used.

Analysis and reaction results of the obtained silica composite are shown in Table 2.

Example 15

In this example, diammonium hydrogen phosphate was supported by a dried product by the impregnation method.

A dried product was produced in the same way as in Example 1 except that the zeolite was changed to 300 g of ZSM-5 ($SiO_2/Al_2O_3$ ratio (by mol)=240). 500 g of an aqueous solution containing 9.0 g of diammonium hydrogen phosphate was added to 500 g of this dried product. The dried product formed slurry without maintaining its powdery state. This slurry was transferred to a flask and dried under reduced pressure at 90° C. using an evaporator. This supporting method applies to phosphorus source supporting method A* in Table 2. This dried product adhered to the inner surface of the flask and was thus laboriously collected. The collected dried product was calcined at 700° C. for 1 hour. This calcined product was acid-washed to produce a silica composite.

Analysis and reaction results of the obtained silica composite are shown in Table 2.

Example 16

Diammonium hydrogen phosphate was supported by zeolite in the same way as in Example 9 so that ZSM-5 ($SiO_2/Al_2O_3$ ratio (by mol)=240) maintained its powdery state. The resulting zeolite was calcined at 600° C. for 1 hour. This calcined product was in an agglomerated form having an average particle size of approximately 15 μm.

A silica composite was produced in the same way as in Example 9 except that this phosphorus-containing ZSM-5 in an agglomerated form was directly used.

Analysis and reaction results of the obtained silica composite are shown in Table 2.

Figure 3:
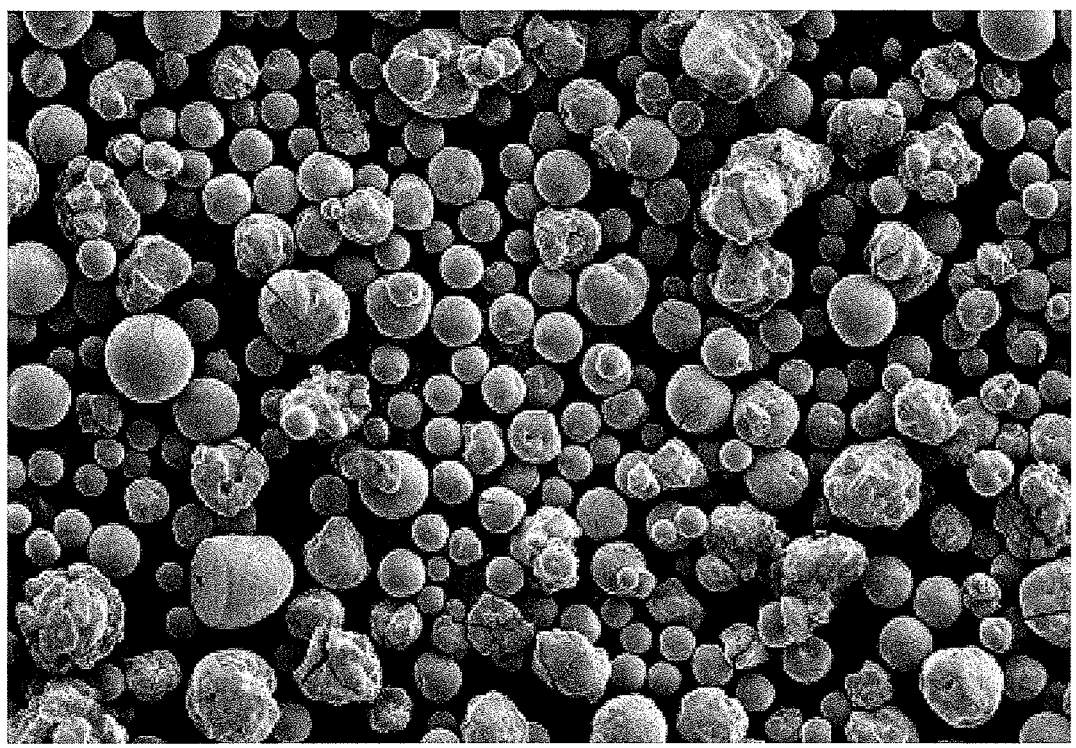
FIG. 3 shows an electron micrograph of a silica composite of Example 16 (magnification: 150 times).

FIG. 3 shows an electron micrograph of the silica composite obtained in Example 16 (magnification: 150 times). As is evident from FIG. 3, the silica composite of Example 16 had rough particle surface and contained a large number of nonspherical particles, compared with the particles of Example 1 (FIG. 1) and Example 2 (FIG. 2).

Example 17

A silica composite was produced in the same way as in Example 1 except that: the amount of diammonium hydrogen phosphate was changed to 12.5 g; and the calcined product was not acid-washed.

Analysis and reaction results of the obtained silica composite are shown in Table 2.

Example 18

A silica composite was produced in the same way as in Example 1 except that: 50 g of zeolite of CHA type (SAPO-34 manufactured by JGC Catalysts and Chemicals Ltd.) and 250 g of ZSM-5 ($SiO_2/Al_2O_3$ ratio (by mol)=27) were mixed and used as the zeolite; and the amount of diammonium hydrogen phosphate was changed to 3.1 g.

Analysis and reaction results of the obtained silica composite are shown in Table 2.

Example 19

The fluidized-bed reaction was performed for 52 hours using the silica composite of Example 4. Then, the catalyst was calcined at 580° C. for 1 hour in an oxygen-containing atmosphere for removal of coke to regenerate the catalyst. The fluidized-bed reaction was performed again under the reaction conditions of Example 4 using this regenerated catalyst. The regenerated catalyst had an initial ethylene conversion rate (at the 3rd hour of the reaction) of 85.2% and thus had activity improved from that of Example 4. The propylene yield was the same as that in Example 4.

Example 20

The silica composite produced in Example 5 was compression-molded and then pulverized to obtain particles having a 6- to 16-mesh size. 8.56 g of this silica composite was loaded into a stainless fixed-bed reaction tube. This silica composite was treated with steam under conditions involving 650° C., 24 hours, a steam partial pressure of 0.8 atmospheres, and a nitrogen gas partial pressure of 0.2 atmospheres. Then, ethylene at 5.8 g/hr, hydrogen at 0.4 g/hr, water at 2.8 g/hr, and nitrogen at 3.1 g/hr were circulated in the reactor, while reaction was performed at a reaction temperature of 550° C., a reaction pressure of 0.14 MPa (gage pressure), and a WHSV of 0.7 $hr^{-1}$ (based on the silica composite). The catalyst had an initial ethylene conversion rate (at the 3rd hour of the reaction) of 78.5% and offered a propylene yield of 30.1% (ethylene conversion rate: 70%).

Example 21

23.0 g of the silica composite produced in Example 6 was loaded into a stainless fluidized-bed reactor having an inside diameter of 1 inch. Then, bioethanol (industrial product) at 21.6 g/hr and nitrogen at 6.5 g/hr were circulated in the reactor, while reaction was performed at a reaction temperature of 550° C., a reaction pressure of 0.14 MPa (gage pressure), and a WHSV of 0.6 $hr^{-1}$ (based on the silica composite). The catalyst had an initial ethanol conversion rate (at the 3rd hour of the reaction) of 100%, which was still 100% even at the 70th hour. The propylene yield was 27.0%.

Example 22

23.0 g of the silica composite produced in Example 12 was loaded into a stainless fluidized-bed reactor having an inside diameter of 1 inch. Then, methanol (manufactured by Wako Pure Chemical Industries, Ltd., special-grade reagent) at 21.4 g/hr and nitrogen at 4.7 g/hr were circulated in the reactor, while reaction was performed at a reaction temperature of 550° C., a reaction pressure of 0.14 MPa (gage pressure), and a WHSV of 0.4 $hr^{-1}$ (based on the silica composite). The catalyst had an initial methanol conversion rate (at the 3rd hour of the reaction) of 100%, which was still 100% even at the 90th hour. At this point in time, the propylene yield was 29.5%.

Example 23

The silica composite produced in Example 12 was compression-molded and then pulverized to obtain particles having a 6- to 16-mesh size. 8.56 g of this silica composite was loaded into a stainless fixed-bed reaction tube. This silica composite was treated with steam under conditions involving 650° C., 24 hours, a steam partial pressure of 0.8 atmospheres, and a nitrogen gas partial pressure of 0.2 atmospheres. Then, methanol (manufactured by Wako Pure Chemical Industries, Ltd., special-grade reagent) at 13.3 g/hr and nitrogen at 3.1 g/hr were circulated in the reactor, while reaction was performed at a reaction temperature of 550° C., a reaction pressure of 0.14 MPa (gage pressure), and a WHSV of 0.7 hr$^{-1}$ (based on the silica composite). The catalyst had an initial methanol conversion rate (at the 3rd hour of the reaction) of 100%, which was still 100% even at the 30th hour. The propylene yield was 42.0%.

Example 24

The silica composite produced in Example 12 was compression-molded and then pulverized to obtain particles having a 6- to 16-mesh size. 8.56 g of this silica composite was loaded into a stainless fixed-bed reaction tube. This silica composite was treated with steam under conditions involving 650° C., 24 hours, a steam partial pressure of 0.8 atmospheres, and a nitrogen gas partial pressure of 0.2 atmospheres. Then, dimethyl ether (manufactured by TOKYO CHEMICAL INDUSTRY CO., LTD.) at 9.5 g/hr and nitrogen at 3.1 g/hr were circulated in the reactor, while reaction was performed at a reaction temperature of 550° C., a reaction pressure of 0.14 MPa (gage pressure), and a WHSV of 0.7 hr$^{-1}$ (based on the silica composite). The catalyst had an initial dimethyl ether conversion rate (at the 3rd hour of the reaction) of 100%, which was still 100% even at the 30th hour. The propylene yield was 40.0%.

Example 25

A phosphorus source was sprayed to zeolite in the same way as in Example 9 (phosphorus source supporting method C) except that: 500 g of ZSM-5 ($SiO_2/Al_2O_3$ ratio (by mol)=27) was used; and 200 g of an aqueous solution containing 38.7 g of diammonium hydrogen phosphate was used. In this case, the zeolite maintained its powdery state. This zeolite was calcined and then pulverized in the same way as in Example 9.

300 g of the phosphorus-containing ZSM-5 thus pulverized was mixed with 882 g of colloidal silica (manufactured by Nalco Company, trade name "NalcoDVZSN006") to prepare a raw material mixture. Then, water was evaporated therefrom to form cake. This cake was extruded into a diameter of 2 mm and a length of 5 mm using an extrusion machine (manufactured by Fuji Paudal Co., Ltd., model: MG-55). The resulting product was dried at 120° C. for 6 hours to obtain a dried product. The obtained dried product was calcined at 700° C. for 1 hour to obtain a silica composite. This silica composite had a phosphorus content of 0.8% by mass based on the total mass of the silica composite. This silica composite had a corrosion index of 6000.

Comparative Example 1

A silica composite was produced in the same way as in Example 1 except that the source of the phosphorus was changed to 94 g of diammonium hydrogen phosphate.

Analysis results of the obtained silica composite are shown in Table 3.

Figure 6:
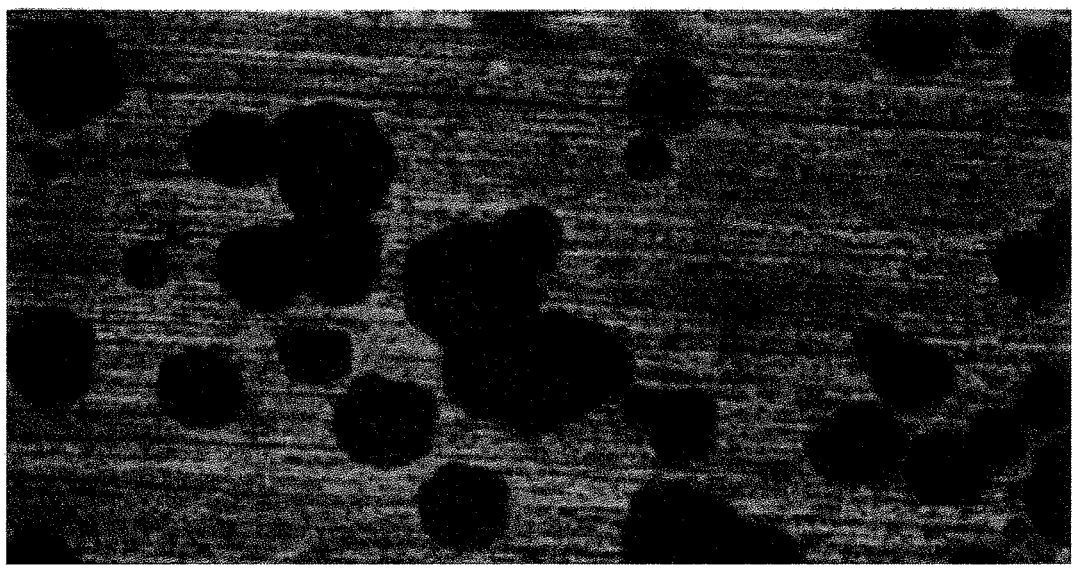
FIG. 6 shows a micrograph of a specimen after a corrosion test of Comparative Example 1 (magnification: 120 times).

FIG. 6 shows a micrograph of a SUS304 specimen after corrosion test using the silica composite of Comparative Example 1 (magnification: 120 times). As is evident from FIG. 6, pits (black portions) were formed by corrosion on the surface of the specimen, demonstrating that the silica composite of Comparative Example 1 had high corrosive effect.

Comparative Example 2

A silica composite was produced in the same way as in Example 1 except that the source of the phosphorus was changed to 40 g of phosphoric acid.

Analysis results of the obtained silica composite are shown in Table 3.

Figure 7:
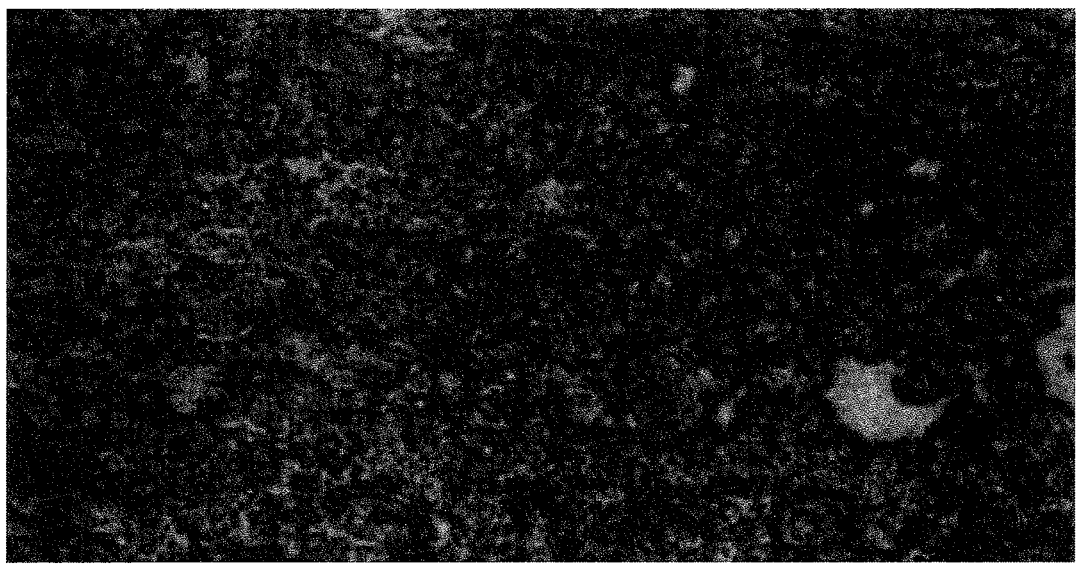
FIG. 7 shows a micrograph of a specimen after a corrosion test of Comparative Example 2 (magnification: 120 times).

FIG. 7 shows a micrograph of a SUS304 specimen after corrosion test using the silica composite of Comparative Example 2 (magnification: 120 times). As is evident from FIG. 7, corrosion occurred on the overall surface of the specimen, demonstrating that the silica composite of Comparative Example 2 had high corrosive effect.

Comparative Example 3

A silica composite was produced in the same way as in Example 1 except that: the colloidal silica was changed to 812 g of trade name "Nalco 2326" manufactured by Nalco Company; 1781 g of alumina sol (manufactured by NISSAN CHEMICAL INDUSTRIES, LTD., trade name "Alumina Sol-100", alumina content: 10% by mass) was added to the raw material mixture; and the phosphorus source was changed to 94 g of diammonium hydrogen phosphate.

Analysis and reaction results of the obtained silica composite are shown in Table 3.

Figure 4:
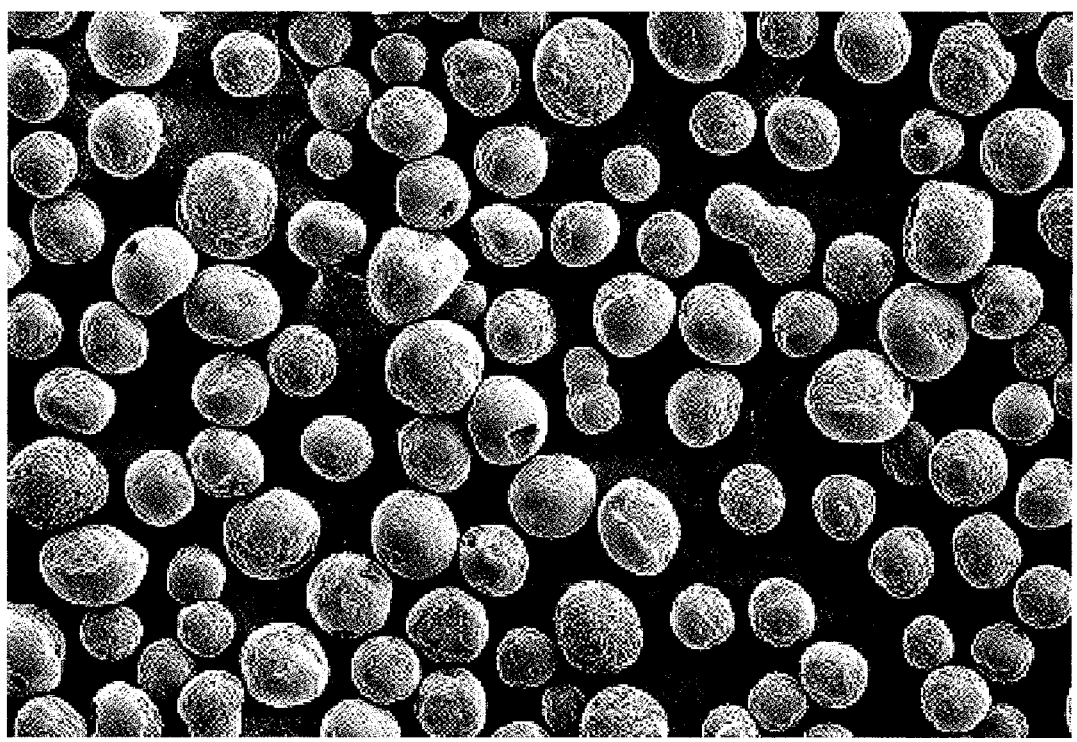
FIG. 4 shows an electron micrograph of a silica composite of Comparative Example 3 (magnification: 150 times).

FIG. 4 shows an electron micrograph of the silica composite obtained in Comparative Example 3 (magnification: 150 times). As is evident from FIG. 4, the silica composite of Comparative Example 4 had a deformed particle shape and depressions on the surface, and its shape was far from smooth.

Comparative Example 4

A silica composite was produced in the same way as in Example 1 except that no phosphate was supported by the silica composite.

Analysis and reaction results of the obtained silica composite are shown in Table 3.

Comparative Example 5

85 g of zeolite of H—Y type (manufactured by TOSOH CORP., $SiO_2/Al_2O_3$ ratio (by mol)=2.5), 85 g of H-ZSM-5 ($SiO_2/Al_2O_3$ ratio (by mol)=50, ion-exchanged into H type in advance with dilute nitric acid), 1803 g of alumina sol (manufactured by NISSAN CHEMICAL INDUSTRIES, LTD., trade name "Alumina Sol-100", alumina content: 10% by mass), 190 g of kaolin (manufactured by Engelhard Corp., trade name "ASP-600"), and 145 g of diammonium hydrogen phosphate (manufactured by Wako Pure Chemical Industries, Ltd., special-grade reagent, solubility in 100 g of water: 131 g (15° C.)) were mixed to prepare a raw material mixture, which was then spray-dried in the same way as in Example 1. This dried product was calcined at 600° C. for 1 hour to obtain a silica composite.

Analysis and reaction results of the obtained silica composite are shown in Table 3.

TABLE 1

|  | Example 1 | Example 2 | Example 3 | Example 4 | Example 5 | Example 6 | Example 7 | Example 8 | Example 9 |
|---|---|---|---|---|---|---|---|---|---|
| Zeolite type | ZSM-5 | ZSM-5 | ZSM-5 | ZSM-5 | ZSM-5 | ZSM-5 | ZSM-5 | ZSM-5 | ZSM-5 |
| $SiO_2/Al_2O_3$ ratio (by mol) of zeolite | 27 | 480 | 50 | 156 | 210 | 280 | 240 | 240 | 240 |
| Phosphorus source | $(NH_4)_2HPO_4$ | $(NH_4)_2HPO_4$ | $NH_4H_2PO_4$ | $(NH_4)_3PO_4$ | $NaH_2PO_4 \cdot 2H_2O$ | $KH_2PO_4$ | $(NH_4)_2HPO_4$ | $(NH_4)_2HPO_4$ | $(NH_4)_2HPO_4$ |
| Phosphorus source supporting method | A | A | A | A | A | A | A | B | C |
| Composition of silica composite |  |  |  |  |  |  |  |  |  |
| Zeolite (wt %) | 49.5 | 50.0 | 49.5 | 49.9 | 49.9 | 50.0 | 49.9 | 49.9 | 49.9 |
| Silica (wt %) | 49.5 | 49.9 | 49.5 | 49.9 | 49.9 | 49.9 | 49.8 | 49.8 | 49.8 |
| Alumina (wt %) | 0.0 | 0.0 | 0.0 | 0.0 | 0.0 | 0.0 | 0.0 | 0.0 | 0.0 |
| Clay mineral (wt %) | 0.0 | 0.0 | 0.0 | 0.0 | 0.0 | 0.0 | 0.0 | 0.0 | 0.0 |
| Phosphorus (wt %) | 1.0 | 0.1 | 1.0 | 0.2 | 0.2 | 0.1 | 0.3 | 0.3 | 0.3 |
| Physical properties of silica composite |  |  |  |  |  |  |  |  |  |
| Bulk density (g/cc) | 0.90 | 0.86 | 0.88 | 0.88 | 0.88 | 0.85 | 0.90 | 0.90 | 0.89 |
| Attrition loss (wt %) | 0.15 | 0.40 | 0.25 | 0.16 | 0.40 | 0.25 | 0.20 | 0.22 | 0.26 |
| Corrosion index | 4,000 | ND | 4,500 | ND | ND | ND | ND | 5,000 | 2,000 |
| Fluidized-bed reaction |  |  |  |  |  |  |  |  |  |
| Initial ethylene conversion rate (%) | 90.2 | 69.5 | 82.3 | 81.5 | 71.8 | 71.0 | 81.0 | 78.5 | 79.3 |
| Propylene yield (%) | 24.0 | 27.0 | 24.5 | 25.5 | 26.5 | 27.5 | 27.3 | 27.0 | 27.4 |

(Note)
A represents that the phosphorus source was supported by the dried product.
B represents that the phosphorus source was added to the raw material mixture.
C represents that the phosphorus source was supported by the zeolite.
ND represents that no corrosion occurred.
Initial ethylene conversion rate represents an ethylene conversation rate at the 3rd hour of the reaction.
Propylene yield represents a propylene yield at an ethylene conversion rate around 70%.
The components other than phosphorus in the composition of the silica composite were indicated in the number rounded off to the first decimal place.

TABLE 2

|  | Example 10 | Example 11 | Example 12 | Example 13 | Example 14 | Example 15 | Example 16 | Example 17 | Example 18 |
|---|---|---|---|---|---|---|---|---|---|
| Zeolite type | ZSM-5 | ZSM-5 | ZSM-5 | ZSM-5 | ZSM-5 | ZSM-5 | ZSM-5 | ZSM-5 | SAPO-34 + ZSM-5 |
| $SiO_2/Al_2O_3$ ratio (by mol) of zeolite | 27 | 10000 | 1000 | 240 | 240 | 240 | 240 | 27 | 27 |
| Phosphorus source | $(NH_4)_2HPO_4$ | $(NH_4)_2HPO_4$ | $(NH_4)_2HPO_4$ | $H_3PO_4$ | $(NH_4)_2HPO_4$ | $(NH_4)_2HPO_4$ | $(NH_4)_2HPO_4$ | $(NH_4)_2HPO_4$ | $(NH_4)_2HPO_4$ |
| Phosphorus source supporting method | A | C | B | A | C* | A* | C | A | A |
| Composition of silica composite |  |  |  |  |  |  |  |  |  |
| Zeolite (wt %) | 51.2 | 50.0 | 50.0 | 49.9 | 49.9 | 49.9 | 49.9 | 49.8 | 50.0* |
| Silica (wt %) | 36.5 | 50.0 | 50.0 | 49.8 | 49.8 | 49.8 | 49.8 | 49.7 | 49.9 |
| Alumina (wt %) | 2.1 | 0.0 | 0.0 | 0.0 | 0.0 | 0.0 | 0.0 | 0.0 | 0.0 |
| Clay mineral (wt %) | 9.7 | 0.0 | 0.0 | 0.0 | 0.0 | 0.0 | 0.0 | 0.0 | 0.0 |
| Phosphorus (wt %) | 0.5 | 0.01 | 0.05 | 0.3 | 0.3 | 0.3 | 0.3 | 0.5 | 0.1 |
| Physical properties of silica composite |  |  |  |  |  |  |  |  |  |
| Bulk density (g/cc) | 0.81 | 0.90 | 0.89 | 0.88 | 0.75 | 0.84 | 0.72 | 0.86 | 0.89 |
| Attrition loss (wt %) | 0.65 | 0.33 | 0.25 | 0.22 | 1.90 | 0.65 | 2.20 | 0.21 | 0.15 |
| Corrosion index | ND | ND | ND | 9,000 | 4,000 | 2,000 | 4,500 | 3,000 | ND |

TABLE 2-continued

|  | Example 10 | Example 11 | Example 12 | Example 13 | Example 14 | Example 15 | Example 16 | Example 17 | Example 18 |
|---|---|---|---|---|---|---|---|---|---|
| Fluidized-bed reaction | | | | | | | | | |
| Initial ethylene conversion rate (%) | 89.5 | 48.0 | 58.3 | 80.5 | 78.0 | 79.3 | 78.5 | 80.3 | 85.5 |
| Propylene yield (%) | 24.0 | 22.4 | 24.0 | 27.0 | 27.0 | 27.3 | 27.0 | 24.2 | 24.0 |

(Note)
A represents that the phosphorus source was supported by the dried product.
B represents that the phosphorus source was added to the raw material mixture.
C represents that the phosphorus source was supported by the zeolite.
ND represents that no corrosion occurred.
Initial ethylene conversion rate represents an ethylene conversation rate at the 3rd hour of the reaction.
Propylene yield represents a propylene yield at an ethylene conversion rate around 70%, provided that the highest propylene yield in the obtained reaction results was shown when the initial ethylene conversion rate was less than 70%.
*represents the total of SAPO-34 and ZSM-5. The components other than phosphorus in the composition of the silica composite were indicated in the number rounded off to the first decimal place.

TABLE 3

|  | Comparative Example 1 | Comparative Example 2 | Comparative Example 3 | Comparative Example 4 | Comparative Example 5 |
|---|---|---|---|---|---|
| Zeolite type | ZSM-5 | ZSM-5 | ZSM-5 | ZSM-5 | HY + ZSM-5 |
| $SiO_2/Al_2O_3$ ratio (by mol) of zeolite | 27 | 27 | 27 | 27 | 2.5/50 |
| Phosphorus source | $(NH_4)_2HPO_4$ | $H_3PO_4$ | $(NH_4)_2HPO_4$ | — | $(NH_4)_2HPO_4$ |
| Phosphorus source supporting method | A | B | A | — | B |
| Composition of silica composite | | | | | |
| Zeolite (wt %) | 48.5 | 49.1 | 48.5 | 50.0 | 30.0* |
| Silica (wt %) | 48.5 | 49.1 | 19.7 | 50.0 | 0.0 |
| Alumina (wt %) | 0.0 | 0.0 | 28.8 | 0.0 | 32.0 |
| Clay mineral (wt %) | 0.0 | 0.0 | 0.0 | 0.0 | 33.0 |
| Phosphorus (wt %) | 3.0 | 1.8 | 3.0 | 0.0 | 5.0 |
| Physical properties of silica composite | | | | | |
| Bulk density (g/cc) | 0.88 | 0.80 | 0.70 | 0.86 | 0.60 |
| Attrition loss (wt %) | 0.24 | 0.40 | 2.10 | 0.26 | 3.55 |
| Corrosion index | 380,000 | Corrosion on overall surface | 460,000 | — | Corrosion on overall surface |
| Fluidized-bed reaction | | | | | |
| Initial ethylene conversion rate (%) | — | — | 75.5 | 81.3 | 25.6 |
| Propylene yield (%) | | | 21.3 | 23.5 | 12.5 |

(Note)
A represents that the phosphorus source was supported by the dried product. B represents that the phosphorus source was added to the raw material mixture. Corrosion on overall surface represents that corrosion occurred on the overall surface of the specimen. Initial ethylene conversion rate represents an ethylene conversation rate at the 3rd hour of the reaction. Propylene yield represents a propylene yield at an ethylene conversion rate around 70%, provided that the highest propylene yield in the obtained reaction results was shown when the initial ethylene conversion rate was less than 70%.
*represents the total of H-Y type and ZSM-5. The components other than phosphorus in the composition of the silica composite were indicated in the number rounded off to the first decimal place.

As is evident from the results shown in Tables 1 and 2, the silica composites of the present embodiment (Examples 1 to 18) were demonstrated to cause much less corrosion even in corrosion test using a stainless steel specimen. The silica composites of the present embodiment were also demonstrated to have a shape and attrition resistance excellent for catalyst use in fluidized-bed reaction and have excellent catalyst properties resulting in high conversion rates and yields in propylene production reaction.

As is evident from comparison among Examples 7, 8, and 9, the phosphorus source supporting method A (the phosphorus source is supported by the dried product) leads to the smallest corrosive effect, followed by the phosphorus source supporting method C (the phosphorus source is supported by the zeolite; relatively small corrosive effect) and the phosphorus source supporting method B (the phosphorus source is added to the raw material mixture; slightly higher corrosive effect) in this order.

As is also evident from comparison between Examples 7 and 15 and between Examples 9 and 14, the cases of Examples 7 and 9 in which the phosphorus source is supported by the zeolite and/or the dried product so that the zeolite and/or the dried product maintain their powdery states facilitate industrial production by virtue of little adhesion to catalyst preparation apparatuses and also reduce corrosive effect.

As is further evident from comparison between Examples 9 and 16, the case of Example 9 in which the phosphorus source is supported by the zeolite which is subjected to the next step after being pulverized easily produces a silica composite having a favorable shape and sufficient attrition resistance.

By contrast, as is evident from the results shown in Table 3, corrosive effect is sharply increased in a silica composite having a phosphorus content exceeding 1% by mass. A silica composite obtained using a support composed mainly of alumina rather than silica (Comparative Example 3) was demonstrated to have a poor shape, a low bulk density, and low attrition resistance, in addition to increased corrosive effect. Such a silica composite was further demonstrated to result in low propylene yields in propylene production reaction.

As shown in FIG. 8, a phosphorus-containing silica composite (Example 1) was demonstrated to have higher initial reaction activity than that of a phosphorus-free silica composite (Comparative Example 4). Specifically, the silica composite containing phosphorus was demonstrated to be hardly subject to dealumination attributed to steaming treatment (treatment with high-temperature steam) performed before reaction and to have high activity.

The present application is based on Japanese Patent Application (No. 2010-262752) that was filed on Nov. 25, 2010 in the Japan Patent Office. The contents thereof are incorporated herein by reference.

INDUSTRIAL APPLICABILITY

A silica composite obtained by a production method of the present invention can be used preferably as a catalyst for producing propylene in a high-temperature steam atmosphere from a hydrocarbon source containing at least one component selected from the group consisting of ethylene, ethanol, methanol, and dimethyl ether.

The invention claimed is:

1. A method for producing a silica composite comprising the steps of:
    preparing a raw material mixture containing silica and zeolite;
    drying the raw material mixture to obtain a dried product; and
    calcining the dried product,
    wherein the method comprises the step of bringing a solution of phosphate into contact with the zeolite and/or the dried product to thereby adjust a phosphorus content in the silica composite to 0.01 to 1.0% by mass based on the total mass of the silica composite,
    a source of the phosphorus is phosphate, and
    the zeolite is of MFI type and has a $SiO_2/Al_2O_3$ ratio (by mol) of 20 or more.

2. The method for producing the silica composite according to claim 1, wherein the step of bringing the solution of phosphoric acid and/or phosphate into contact with the zeolite and/or the dried product comprises adjusting the amount of the solution of phosphoric acid and/or phosphate so that the zeolite and/or the dried product maintain their powdery states.

3. The method for producing the silica composite according to claim 1 or 2, further comprising the step of pulverizing the zeolite after the step of bringing the solution of phosphate into contact with the zeolite.

4. The method for producing the silica composite according to claim 1 or 2, wherein the phosphorus content in the silica composite is 0.01 to 0.5% by mass based on the total mass of the silica composite.

5. The method for producing the silica composite according to claim 1 or 2, further comprising the step of bringing a calcined product obtained in the calcining step into contact with an acidic liquid after calcining the dried product.

6. The method for producing the silica composite according to claim 1 or 2, wherein the silica composite is substantially free from aluminum not in zeolite.

* * * * *